(12) United States Patent
Cao et al.

(10) Patent No.: US 11,918,377 B2
(45) Date of Patent: Mar. 5, 2024

(54) DRY ELECTRODES IN A WEARABLE GARMENT

(71) Applicant: Medtronic, Inc., Minneapolis, MN (US)

(72) Inventors: Jian Cao, Shoreview, MN (US); Arthur K. Lai, Minnetonka, MN (US); Laura A. Chicos, River Forest, IL (US); Paul J. DeGroot, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 447 days.

(21) Appl. No.: 17/152,328

(22) Filed: Jan. 19, 2021

(65) Prior Publication Data

US 2022/0225937 A1 Jul. 21, 2022

(51) Int. Cl.
*A61B 5/00* (2006.01)
*A61B 5/05* (2021.01)
(Continued)

(52) U.S. Cl.
CPC ............ *A61B 5/6804* (2013.01); *A61B 5/053* (2013.01); *A61B 5/0816* (2013.01); *A61B 5/282* (2021.01);
(Continued)

(58) Field of Classification Search
CPC ..... A61B 5/282; A61B 5/6804; A61B 5/0006; A61B 5/0205; A61B 5/318; A61B 5/6805;
(Continued)

(56) References Cited

U.S. PATENT DOCUMENTS

| 5,810,015 A | 9/1998 | Flaherty |
| 5,954,058 A | 9/1999 | Flaherty |

(Continued)

FOREIGN PATENT DOCUMENTS

| CN | 103622688 A | 3/2014 |
| CN | 108092544 A | 5/2018 |

(Continued)

OTHER PUBLICATIONS

Lidón-Roger et al. "Textile Concentric Ring Electrodes for ECG Recording Based on Screen-Printing Technology" Sensors 2018, 18, 300; doi:10.3390. (Year: 2018).*

(Continued)

*Primary Examiner* — Joseph A Stoklosa
*Assistant Examiner* — Brian M Antiskay
(74) *Attorney, Agent, or Firm* — Shumaker & Sieffert, P.A.

(57) ABSTRACT

A wearable garment and an arrangement of electrodes configured to measure bioelectrical signals from a patient. The dry electrodes are free from adhesives to hold the electrodes in place on the patient's skin. The arrangement of the electrodes may be configured to limit noise and facilitate accurate signal sensing from the patient even with some amount of relative movement between the electrodes and the patient's skin. The wearable garment may be controllable to change the amount of compression based on the sensed signals from the electrodes, and from other sensors. The garment may maintain a comfortable level of compression until processing circuitry detects a signal of interest, such as a cardiac arrhythmia, irregular respiration, or some other signal. The processing circuitry may cause the wearable garment to increase compression to improve the contact between the electrodes and the patient's skin and improve reception of the measured signals.

18 Claims, 11 Drawing Sheets

(51) Int. Cl.
  *A61B 5/053* (2021.01)
  *A61B 5/08* (2006.01)
  *A61B 5/282* (2021.01)
  *A61B 5/308* (2021.01)

(52) U.S. Cl.
  CPC ............ *A61B 5/308* (2021.01); *A61B 5/6843* (2013.01); *A61B 5/7207* (2013.01); *A61B 5/7225* (2013.01); *A61B 5/725* (2013.01); *A61B 2562/06* (2013.01)

(58) Field of Classification Search
  CPC ............ A61B 2560/0412; A61B 5/053; A61B 5/6823; A61B 5/02438; A61B 5/0245; A61B 5/6831; A61B 5/332; A61B 5/287; A61B 5/1118; A61B 5/0816; A61B 5/308; A61B 5/0531; A61B 2562/04; A61B 5/305; A61B 5/6801; A61B 2018/00839; A61B 2562/125
  USPC ........ 600/372, 382–384, 386, 388–390, 393, 600/506, 508–509
  See application file for complete search history.

(56) References Cited

U.S. PATENT DOCUMENTS

| | | | |
|---|---|---|---|
| 6,532,379 | B2 | 3/2003 | Stratbucker |
| 8,217,523 | B2 | 7/2012 | Brown et al. |
| 8,591,430 | B2 | 11/2013 | Amurthur et al. |
| 8,644,925 | B2 | 2/2014 | Volpe et al. |
| 8,680,751 | B2 | 3/2014 | Wang et al. |
| 8,777,863 | B2 | 7/2014 | Piaget et al. |
| 9,026,212 | B2 | 5/2015 | Imran |
| 9,364,675 | B2 | 6/2016 | Deterre et al. |
| 9,511,237 | B2 | 12/2016 | Deterre et al. |
| 9,748,872 | B2 | 8/2017 | Al Ahmad et al. |
| 9,847,739 | B2 | 12/2017 | Deterre et al. |
| 9,872,757 | B2 | 1/2018 | Kelly et al. |
| 9,884,180 | B1 | 2/2018 | Ho et al. |
| 10,027,254 | B2 | 7/2018 | Ardanuc et al. |
| 10,044,218 | B2 | 8/2018 | Tiefnig |
| 10,130,823 | B2 | 11/2018 | Kaib et al. |
| 10,183,160 | B2 | 1/2019 | Kaib et al. |
| 10,271,791 | B2 | 4/2019 | Donnelly et al. |
| 10,581,344 | B2 | 3/2020 | Cottone et al. |
| 10,716,949 | B2 | 7/2020 | Freeman et al. |
| 10,729,913 | B2 | 8/2020 | Freeman et al. |
| 2005/0113703 | A1* | 5/2005 | Farringdon ............ A61B 5/021 600/509 |
| 2009/0216192 | A1 | 8/2009 | Schriver et al. |
| 2010/0171394 | A1 | 7/2010 | Glenn et al. |
| 2010/0171395 | A1 | 7/2010 | Cannata et al. |
| 2010/0331974 | A1 | 12/2010 | Schaper, Jr. |
| 2011/0304240 | A1 | 12/2011 | Meitav et al. |
| 2012/0158074 | A1 | 6/2012 | Hall |
| 2013/0253285 | A1* | 9/2013 | Bly .................... A61B 5/02055 600/301 |
| 2015/0073251 | A1* | 3/2015 | Mazar ................... A61B 5/318 600/391 |
| 2017/0069823 | A1 | 3/2017 | Karpelson |
| 2017/0354372 | A1 | 12/2017 | Varadan et al. |
| 2018/0235499 | A1 | 8/2018 | Zorman et al. |
| 2018/0235542 | A1* | 8/2018 | Yun ...................... A61B 5/6843 |
| 2018/0272147 | A1 | 9/2018 | Freeman et al. |
| 2019/0000332 | A1 | 1/2019 | Li et al. |
| 2019/0091479 | A1 | 3/2019 | Bonnet |
| 2019/0151666 | A1 | 5/2019 | Bonnet |
| 2019/0192870 | A1 | 6/2019 | Zaidi et al. |
| 2019/0350169 | A1 | 11/2019 | Weinrauch et al. |
| 2019/0381325 | A1 | 12/2019 | Regnier et al. |
| 2019/0393406 | A1 | 12/2019 | Chen et al. |
| 2020/0038671 | A1 | 2/2020 | Schulhauser et al. |
| 2020/0046962 | A1 | 2/2020 | Lu et al. |
| 2020/0069953 | A1 | 3/2020 | Finch et al. |
| 2021/0228134 | A1* | 7/2021 | Trapero Martin ..... G16H 20/60 |

FOREIGN PATENT DOCUMENTS

| | | |
|---|---|---|
| CN | 108310649 A | 7/2018 |
| CN | 110212873 A | 9/2019 |
| CN | 210120536 U | 2/2020 |
| WO | 2013182762 A2 | 12/2013 |
| WO | 2016077786 A1 | 5/2016 |
| WO | 2019125156 A1 | 6/2019 |

OTHER PUBLICATIONS

"Energy Harvesting from Moving Organs to Power Medical Implants," from Medgadget dated Jan. 24, 2014, retrieved from https://www.medgadget.com/2014/01/energy-harvesting-from-moving-organs.html on Mar. 30, 2020, 3 pp.

"ZOLL and Myant Enter Strategic Research and Development Collaboration," News Release, Nov. 28, 2017 5 pp.

Barath, H., "New Pacemaker Harvests Energy from the Heart," Scientific American, May 2019, 5 pp. retrieved from https://www.scientificamerican.com/article/new-pacemaker-harvests-energy-from-the-heart/ on Apr. 21, 2021.

Cadei et al., "Kinetic and thermal energy harvesters for implantable medical devices and biomedical autonomous sensors," Measurement Science and Technology, vol. 25, No. 1, Nov. 2013, 14 pp.

Ettinger et al., "Wearable cardioverter defibrillators for the prevention of sudden cardiac arrest: a health technology assessment and patient focus group study," Medical Devices: Evidence and Research; Nov. 2017, 15 pp.

Fukuoka et al., "Development of a Compact Wireless Lapacian Electrode Module for Electromyograms and its Huma Interface Applications," Sensors, vol. 13, No. 2, Feb. 2013, 16 pp.

Hannan et al., "Energy harvesting for the implantable biomedical devices: issues and challenges," BioMedical Engineering OnLine, vol. 13, Article No. 79, Jun. 2014, 23 pp.

Madhusoodanan, J., "Inner Workings—Self-powered biomedical devices tap into the body's movements," Proceedings of the National Academy of Sciences of the United States of America (PNAS), Sep. 2019, vol. 116, No. 36, 3 pp.

Niu et al., "A universal self-charging system driven by random biomechanical energy for sustainable operation of mobile electronics," Nature Communications, vol. 6, Article No. 8975, Dec. 2015, 8 pp.

Ouyang et al., "Symbiotic cardiac pacemaker," Nature Communications, vol. 10, Article No. 1821, Apr. 2019, 10 pp.

Sensor Research; Findings from University of Technology Yields New Data on Sensor Research (Optimization of Reduced Go-based Cotton Electrodes for Wearable Electrocardiography), Dialog, retrieved from https://dialog.proquest.com/professional/docview/2430504603/17348EC29682E00ABC/1?accountid=157282, on Aug. 13, 2020, 2 pp.

U.S. Appl. No. 16/904,477, filed Jun. 17, 2020, naming inventor Gunderson.

U.S. Appl. No. 17/152,364, filed Jan. 19, 2021, naming inventors Cao et al.

* cited by examiner

DRY ELECTRODES IN A WEARABLE GARMENT

TECHNICAL FIELD

This disclosure relates to medical devices, and more particularly, to devices to monitor cardiac rhythm.

BACKGROUND

A number of wearable electronic devices exist that incorporate electrodes for monitoring bioelectric signals. In some examples, a patient may wear an ambulatory electrocardiography device, such as a Holter monitor, ambulatory cardiac monitoring patch, smart watch, or another external cardiac monitoring device, to collect data on the patient's cardiac activity. Such devices may record the patient's heart activity throughout the day and during events, such as sitting, standing, exercise, etc. Other examples of ambulatory measurement devices may monitor the patient for other sensed bioelectrical signals, such as biological impedance.

In other examples, a wearable automated external defibrillator (WAED), also referred to as a wearable cardiac defibrillator (WCD), is an option for patients having an identified risk of malignant tachyarrhythmia, but for whom an implantable cardioverter-defibrillator may not be indicated or desired. Malignant tachyarrhythmia, for example, ventricular fibrillation (VF), is an uncoordinated contraction of the cardiac muscle of the heart. If this arrhythmia continues for more than a few seconds, it may result in cardiogenic shock and stop effective blood circulation. Sudden cardiac death (SCD) may result in a matter of minutes.

In other examples, a wearable automated external defibrillator (WAED), also referred to as a wearable cardiac defibrillator (WCD), is an option for patients having an identified risk of malignant tachyarrhythmia, but for whom an implantable cardioverter-defibrillator may not be indicated or desired. WAEDs typically include straps or a garment carrying its components, such as sensing and defibrillation electrodes, processing circuitry, and shock generation and sensing circuitry, which may allow such components to be worn by a patient. Similar wearable devices may include sensing capability, but not necessarily defibrillation or other therapy delivery capability.

SUMMARY

In general, the disclosure describes a wearable garment and an arrangement of dry electrodes configured to measure signals from a patient. The dry electrodes are free from adhesives, such as conductive gels, to hold the electrodes in place on the patient's skin, which may provide improved comfort for the patient relative to electrodes including adhesives, and therefore may improve patient compliance in wearing the garment with the electrodes. However, dry electrodes may move on the skin and cause noise in the sensed bioelectrical signals. The arrangement of the electrodes of this disclosure may be configured to limit noise and thereby facilitate accurate signal sensing from the patient even with some amount of relative movement between the electrodes and the patient's skin.

In addition, the wearable garment may be controllable to change the amount of compression based on the sensed signals from the electrodes, and from other sensors. A wearable garment with a tight compression may provide improved electrode contact and reduce noise, but may reduce patient comfort, and therefore reduce patient compliance. A patient may decide not to wear a garment that is uncomfortable. The wearable garment of this disclosure may be controllable, such as by processing circuitry included in the garment, to maintain a comfortable level of compression until the processing circuitry detects a signal of interest, such as a cardiac arrhythmia, irregular respiration, or some other signal. The processing circuitry may cause the wearable garment to increase compression to improve the contact between the electrodes and the patient's skin and improve reception of the measured signals. In this disclosure, "in contact" requires the electrode to be touching on the patient's body tissue, such as the surface of the patient's skin.

In one example, this disclosure describes a medical device includes a first electrode, a second electrode, a third electrode, and a fourth electrode, each of the electrodes configured to be placed in contact with skin of a patient and held in position with a compressive member that is free of adhesives, wherein the first electrode and second electrode are configured to output an impedance measurement signal, and wherein the third electrode and the fourth electrode are configured to sense electrocardiogram (ECG) signals from the patient via the third electrode and the fourth electrode.

In another example, this disclosure describes a medical system includes first circuitry configured to measure a voltage, a second circuitry configured output a constant current signal, a medical device includes a first electrode, a second electrode, a third electrode, and a fourth electrode, each of the electrodes configured to be placed in contact with skin of a patient and held in position with a compressive member that is free of adhesives, and sensing circuitry configured to: output an impedance measurement signal via the first electrode and the second electrode; and sense electrocardiogram (ECG) signals from the patient via the third electrode and the fourth electrode.

In another example, this disclosure describes a method includes delivering, by a medical device, an impedance measurement signal via a first electrode and a second electrode; sensing, by the medical device, an electrocardiogram via a third electrode and a fourth electrode, wherein each of the first electrode, the second electrode, the third electrode, and the fourth electrode is configured to be placed in contact with skin of a patient and held in position with a compressive member that is free of adhesives.

In one example, this disclosure describes a method includes receiving, by processing circuitry, an indication from a mechanical sensor of a compression level for a garment, wherein a medical device comprises the garment, the processing circuitry, and the mechanical sensor; setting, by the processing circuitry, the compression level for the garment to a first compression level at a first time, wherein the garment comprises a plurality of electrodes, and wherein the first compression level locates the plurality of electrodes on a patient's skin such that the plurality of electrodes receives bioelectrical signals from a patient; and at a second time, changing, by the processing circuitry, the compression level from the first level to a second compression level based on one or more of: the indication of the compression level from the mechanical sensor and the received bioelectrical signals.

In another example, this disclosure describes a medical device includes a garment configured to be worn by a patient, the garment including: a mechanical sensor configured to output an indication of a compression level of the garment; an apparatus configured to adjust the compression level of the garment; and a plurality of electrodes located on the garment such that the plurality of electrodes receives bioelectrical signals from a patient's skin; processing circuitry attached to the garment and operatively coupled to the mechanical sensor, the plurality of electrodes and the apparatus, wherein the processing circuitry is configured to: receive the indication from the mechanical sensor of the compression level for the garment, set the compression level for the garment to a first compression level at a first time based on the indicated compression level; at a second time, change the compression level from the first compression level to a second compression level based on one or more of: the indication of the compression level from the mechanical sensor and the received bioelectrical signals.

In another example, this disclosure describes a computer-readable medium comprising instructions for causing a programmable processor to: receive an indication, from a mechanical sensor of a medical device, of a compression level for a garment, wherein the medical device comprises the garment, the programmable processor and the mechanical sensor; set the compression level for the garment to a first compression level at a first time, wherein the garment comprises a plurality of electrodes, and wherein the first compression level locates the plurality of electrodes on a patient's skin such that the plurality of electrodes receives bioelectrical signals from a patient; and at a second time different from the first time, change the compression level from the first compression level to a second compression level based on one or more of: the indication of the compression level from the mechanical sensor and the received bioelectrical signals.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
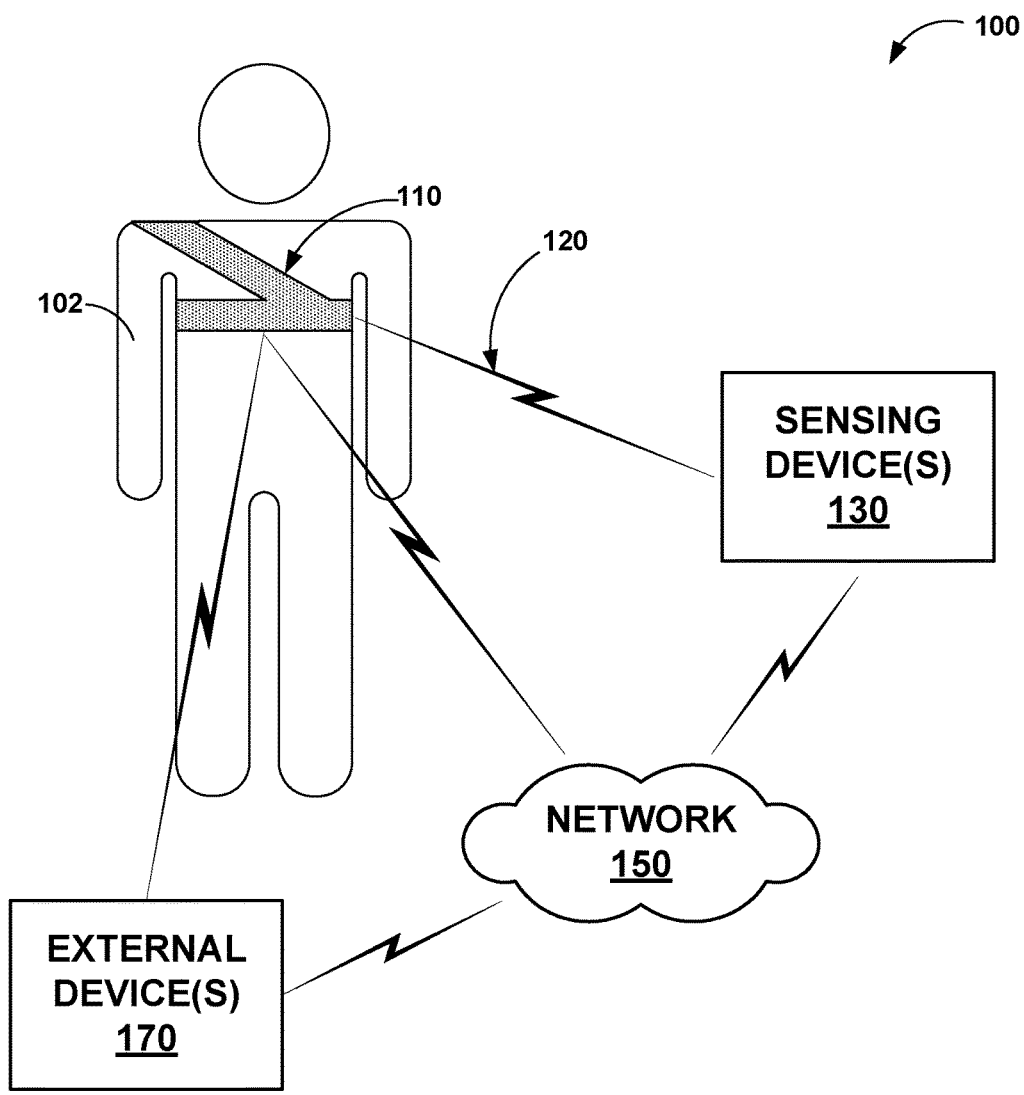
FIG. 1 is a conceptual diagram illustrating an example system that may be used to sense bioelectrical signals from a patient.

FIG. 1 is a conceptual diagram illustrating an example system 100 that may be used to monitor bioelectrical signals from a patient. In some examples, system 100 may deliver therapy to a heart of a patient 102, such as to provide therapy for a cardiac arrhythmia. System 100 may include an apparatus 110, one or more sensing devices 130, a network 150, and one or more external devices 170. Apparatus 110 may be worn by patient 102. Apparatus 110 may include a garment with electronics, devices to adjust the degree of compression of the garment, electrodes, and other components. Apparatus 110 may be configured to monitor bioelectrical signals from patient 102 and may configured to provide therapy. In some examples, apparatus 110 includes one or more sense electrodes configured to sense a phenomenon, e.g., the bioelectrical signal, based on the electrodes in contact with the skin of patient 102. Some examples of bioelectrical, or physiological signals may include bioelectrical impedance, myoelectrical signals, cardiac signals such as electrocardiogram (ECG) or heart sounds and similar signals of patient 102. In some examples, apparatus 110 is a WAED. In other examples, apparatus 110 may be any of a number of wearable electronic devices, including a smart watch, wearable patch, Holter monitor, and so on. In some examples, apparatus 110 may be configured to monitor patient 102 and communicate with external devices 170 either directly or through network 150.

Sensing device(s) 130 may be configured to sense a phenomenon of patient 102 and/or the patient's environment. In some examples, sensing devices 130 may be included as part of apparatus 110. For example, a sensing device including a movement sensor, such as an accelerometer, may be external to apparatus 110, and/or included at some location in the garment that is part of apparatus 110. In some examples, apparatus 110 may be configured to sense the same or different phenomena of patient 102 than sensing device(s) 130 that are external to apparatus 110. As illustrated in FIG. 1, apparatus 110 and sensing device(s) 130 may communicate via one or more links 120. In some examples, links 120 may be Bluetooth® links, such as Bluetooth® Low Energy (BLE) links, or other wired or wireless protocols.

In some examples, apparatus 110 will wake up a sensing device 130 using a specified magnetic, radio-frequency (RF), or electrical signal. In some examples, once a connection is established between apparatus 110 and sensing device 130, periodic advertisements may maintain the connection. In some examples, organizational or globally unique identifiers may be used by apparatus 110 to distinguish among sensing devices 130. In some examples, communication between apparatus 110 and sensing devices 130 may generally by according to the Bluetooth®, BLE or similar protocols.

Network 150 may represent any single network or combination of networks that facilitate communication between devices. As one example, network 150 may represent a combination of wireless and wired networks (e.g., the Internet) that facilitate communication between one or more external devices 170 and apparatus 110 (and/or sensing devices 130). External devices 170 and network 150 may comprise a remote patient monitoring system, such as the Carelink® network, available from Medtronic Inc., of. In some examples, external device(s) 170 may include one or more servers, and one or more personal computers, e.g., a computer that a healthcare provider may interact with via a user interface. In some examples, system 100 includes multiple external devices 170 (e.g., a remote patient monitoring system and one or more personal computers). In some examples, external device(s) 170 may comprise a cloud-based computing system.

External devices 170 may be configured to receive patient data from apparatus 110 and/or sensing devices 130 and store the data in memory. External device 170 may store data collected from populations of patients. In some examples the population data includes information about patient 102, but in other examples the population data does not necessarily include information about patient 102.

Figure 2A:
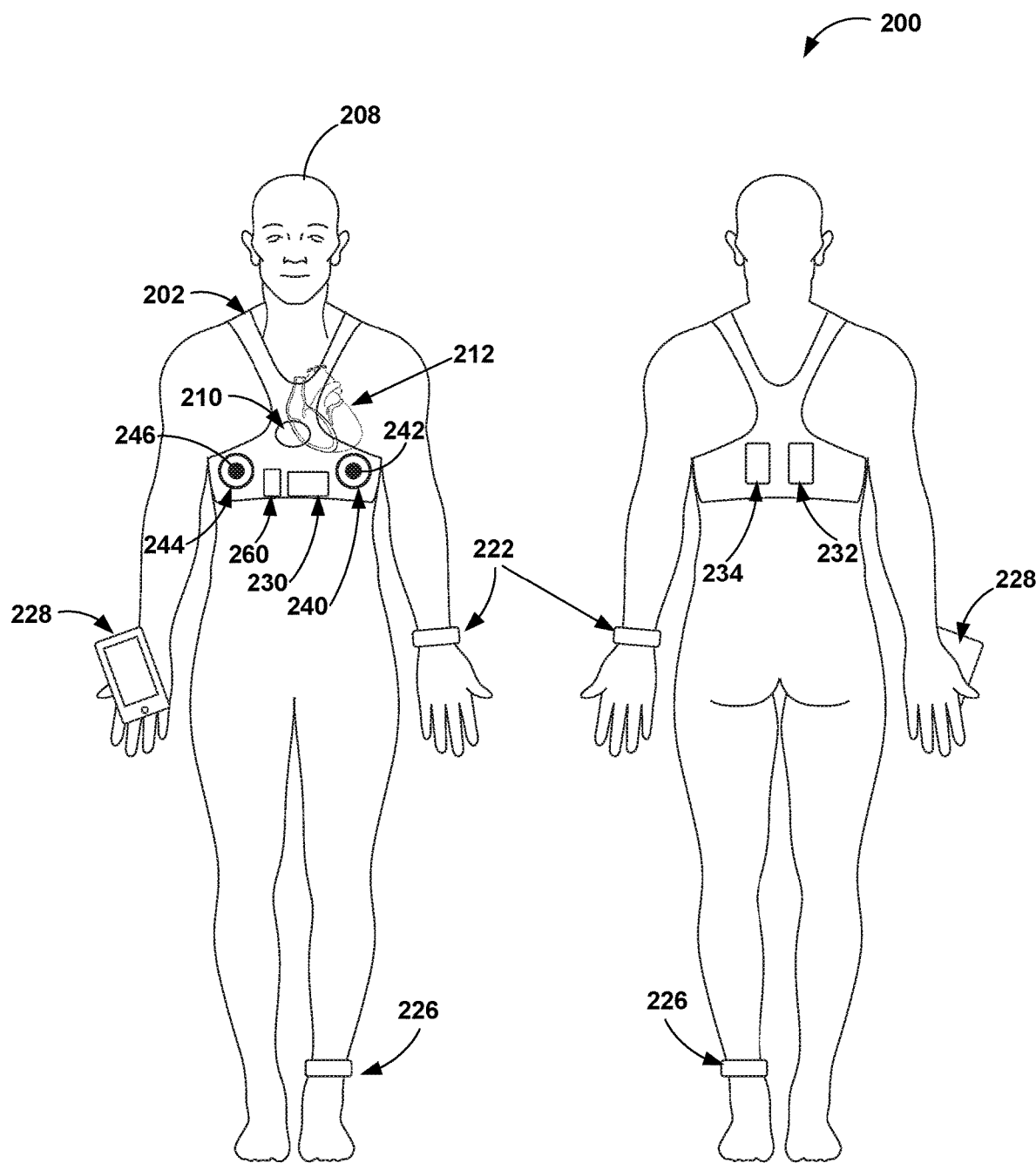
FIG. 2A is a conceptual diagram illustrating a wearable garment configured to sense bioelectrical signals from a patient.

FIG. 2A is a conceptual diagram illustrating an example wearable garment configured to sense bioelectrical signals from a patient. System 200 in the example of FIG. 2A is an example of system 100 described above in relation to FIG. 1. In the example of FIG. 2A, system 200 includes wearable garment 202, one or more other wearable devices 222 and 226 and a portable computing device 228.

Wearable garment 202 is a medical device that, in the example of FIG. 2A, includes a plurality of sensing electrodes 240, 242, 244, 246 located on the garment such that the plurality of sensing electrodes receives bioelectrical signals from the skin of patient 208. Garment 202 also includes processing circuitry 210 and therapy delivery electrodes 230, 232 and 234. In some examples, garment 202 may include a mechanical sensor configured to output an indication of a compression level of garment 202 and an apparatus configured to adjust the compression level of the garment (not shown in FIG. 2A). Power source 260 may provide power to the components of wearable garment 202. In some examples power source 260 may be a replaceable or rechargeable battery. In some examples, power source 260 may be mounted on garment 202. In other examples, power source 260 may be carried externally and connected to garment 202, e.g., carried in a separate belt pack, a purse, and so on.

Processing circuitry 210 may be attached to garment 202 and operatively coupled to the mechanical sensor, the sensing electrodes 240, 242, 244 and 246, and the apparatus for adjusting the compression level of garment 202. Processing circuitry 210 may be configured to receive the indication from the mechanical sensor of the current compression level for garment 202 and control the apparatus for adjusting the compression level to maintain a target compression level. In some examples, each patient may have different body size and the target compression level of garment 202 may be adjusted to accommodate different sizes of patient. Processing circuitry 210 may set the compression level for the garment to a first compression level at a first time and a second compression level at a second time. In some examples, the first compression level may be set such that the sensing electrodes may be placed in contact with skin of patient 208 and held in position such that the sensing electrodes may measure bioelectrical signals from patient 208. The first compression level may be such that the priority is patient comfort at the expense of a looser contact between the patient's skin and the sensing electrodes. At the first compression level, sensing electrodes 240, 242, 244 and 246 may move relative to the skin of patient 208 and cause some noise in the received bioelectrical signals but provide a higher level of comfort for patient 208. Therefore, patient 208 may be more inclined to wear garment 202 more regularly.

When desired, e.g., when processing circuitry 210 receives bioelectrical signals indicating a cardiac arrhythmia, a lead off or disconnected condition, or some other predetermined condition, processing circuitry 210 may signal the apparatus to change the compression level to a second, tighter compression level when compared to the first compression level. For the tighter compression level, the priority may shift from patient comfort to improved contact between sensing electrodes 240, 242, 244 and 246 and the patient's skin. In some examples, for a lead off or noisy signal indication processing circuitry 210 may confirm whether there is an improved signal at the second compression level. In other examples, while at the second compression level, processing circuitry 210 may confirm that the cardiac arrhythmia is treatable by a defibrillation shock and, if necessary, alert patient 208 and deliver the shock.

In some examples, processing circuitry 210 may activate one or more conductive gel release mechanisms prior to delivering the defibrillation shock. In some examples the conductive gel may be contained in flattened, tubular capsules. In some examples, processing circuitry 210 may increase the compressive force such that the compression of garment 202 causes the capsule to release the gel. In other examples, processing circuitry 210 may trigger a mechanical, electrical, or chemical reaction to release gel, or trigger a primer which then releases the gel. In other examples, processing circuitry may activate a mechanism to move a gel capsule from a location that is not in contact with the therapy electrodes or the patient's skin, to a contacting location. For example, processing circuitry 210 may cause gel container to move from initial position, e.g., behind some protective mesh or film to a location in contact with the skin. In some examples the compressive force in one or more locations on garment 202 may cause the gel container, or the protective material, to move to allow the gel to release.

In other examples, therapy delivery electrodes 230, 232 or 234 may comprise non-liquid gel pads, or other similar material, that are positioned so the therapy delivery electrodes do not contact the patient's skin until triggered to do so by processing circuitry 210. In other words, the therapy delivery electrodes may not remain in regular contact with skin but do so only when the garment is compressed, or otherwise triggered, by processing circuitry 210. In some examples, increased garment compression may cause the therapy deliver pads to make mechanical contact with the patient's skin. In some examples, e.g., if processing circuitry fails to confirm a shockable arrhythmia, processing circuitry 210 may cause the therapy delivery pads to move off the patient's skin, e.g., back to a "ready position." In other examples, compression of the garment may move the conductive material of the therapy pads through a porous barrier such that the conductive surface is then in contact with the patient's skin.

In some examples, the conductive gel may disperse under one or more of the therapy delivery electrodes 230, 232 or 234 to improve conduction between the electrode and the patient's skin. In other words, processing circuitry 210 may cause one or more conductive gel compartments associated with one or more therapy delivery electrodes to release conductive gel, prior to delivering electrical stimulation therapy via electrodes 230, 232 or 234. By releasing conductive gel only when needed to deliver electrical stimulation therapy, patient 208 may avoid having to have gel in place during normal daily activity and therefore may improve comfort for patient 208, when compared to having to apply conductive gel or other adhesive, when patient 208 dons garment 202.

In other examples, the mechanical sensor may indicate that the compression level for garment 202 has changed, e.g., to a looser fit. In some examples, the received bioelectrical signals may also indicate a lead off, or increased noise or signal artifacts caused by the looser fit. A changed compression level may result from a relaxation in elastic material of garment 202 over time, patient 208 changes into different clothing, e.g., removes a coat, or for other reasons. Processing circuitry 210 may cause the apparatus of garment 202 to adjust the compression level to balance patient comfort with electrode-to-skin contact based on the indication of the compression level from the mechanical sensor and the received bioelectrical signals by executing an algorithm stored at a memory location operatively coupled to processing circuitry 210.

In some examples, garment 202 may also include a motion sensor, such as an accelerometer or similar sensor (not shown in FIG. 2). One or more motion sensors may be included in processing circuitry 210, and/or located elsewhere in garment 202. The motion sensor of this disclosure may be configured to determine one or more of movement or posture of the patient. For example, patient 208 may increase activity level, such as running, jumping and so on, which may cause increased movement between sensing electrodes 240, 242, 244 and 246 and the patient's skin. Also, patient 208 may change posture from an upright to a sitting or supine position. In some examples, external devices 222 and 226 as well as portable computing device 228 may include sensors that indicate movement, temperature, and so on. Processing circuitry 210 may receive the indication of movement and/or posture of patient 208, and in some examples, may dynamically adjust the compression level of garment 202 based on one or more of the indication of the compression level from the mechanical sensor, the received bioelectrical signals or the indication from the motion sensor.

Processing circuitry 210 may be an example of a programmable processor, which may include any one or more of a microcontroller (MCU), e.g. a computer on a single integrated circuit containing a processor core, memory, and programmable input/output peripherals, a microprocessor (µP), e.g. a central processing unit (CPU) on a single integrated circuit (IC), a controller, a digital signal processor (DSP), an application specific integrated circuit (ASIC), a field-programmable gate array (FPGA), a system on chip (SoC) or equivalent discrete or integrated logic circuitry. A programmable processor may be integrated circuitry, i.e., integrated processing circuitry, and that the integrated processing circuitry may be realized as fixed hardware processing circuitry, programmable processing circuitry and/or a combination of both fixed and programmable processing circuitry. Accordingly, the terms "processing circuitry," "processor" or "controller," as used herein, may refer to any one or more of the foregoing structures or any other structure operable to perform techniques described herein.

Examples of a memory may include any type of computer-readable storage media, such as random access memory (RAM), read only memory (ROM), programmable read only memory (PROM), erasable programmable read only memory (EPROM), electronically erasable programmable read only memory (EEPROM), flash memory, and similar devices. In some examples the computer readable storage media may store instructions that cause the processing circuitry to execute the functions described herein. In some examples, the computer readable storage media may store data, such as configuration information, temporary values and other types of data used to perform the functions of this disclosure.

In the example of FIG. 2A, therapy electrodes 230, 232 and 234 and sensing electrodes 240, 242, 244 and 246 are configured to be placed in contact with skin of a patient and held in position with a compressive member, such as garment 202. Both therapy electrodes 230, 232 and 234 and sensing electrodes 240, 242, 244 and 246 may be free of adhesives. Electrodes held in position only with the compressive force from garment 202 may improve patient comfort when compared to electrodes held in place by adhesives. Though depicted as four sensing electrodes and three therapy electrodes in the example of FIG. 2A, garment 202 may include any number of sensing, or therapy electrodes. The number and location of electrodes may depend on patient anatomy as well as a configuration to provide the best signal quality.

The example of FIG. 2A depicts sensing electrodes 242 and 246 as substantially circular disk shaped electrodes and sensing electrodes 244 and 240 as substantially circular ring shaped electrode surrounding electrodes 242 and 246. For example, FIG. 2A depicts sensing electrode 242 as a disk surrounded by the ring of electrode 240. In other examples, electrodes 240, 242, 244 and 246 may be any substantially circular shape, such as an oval, octagon, or similar shape. In other examples, electrodes 240, 242, 244 and 246 may be other geometric shapes such as square or rectangle. In contrast, other examples of multiple sensing electrodes may have arranged the electrodes that are approximately the same size with equal, or approximately equal spacing between the electrodes.

Electrodes 242 and 240 form a concentric arrangement and may appear to be a Laplacian bipolar type electrode. However, electrodes 242 and 240 connect to the circuitry of system 200 in a completely different manner than the high side and low side of a bipolar type electrode. In this disclosure, electrode 242, as well as electrode 246 connects to circuitry that outputs an impedance measurement signal. In other words, the pair of electrodes 242 and 246 are configured to output the impedance measurement signal. In some examples the impedance measurement signal may be a constant current signal. In other examples, the impedance measurement signal may be a high frequency signal, e.g., approximately 8 kHz-16 kHz.

The third and fourth electrodes 244 and 240 may connect to a high side and low side inputs of an amplifier to measure voltage. In contrast, a bipolar Laplacian electrode would connect the inner disk and outer ring electrodes to the high side and low side of an amplifier to measure voltage. In some examples, the impedance measurement signal may be injected to electrode 242 and return from electrode 246, or vice versa. Sensing circuitry connected to sensing electrodes 240 and 244 may measure the induced voltage in the patient's tissue caused by the impedance measurement signal. The measured induced voltage may provide an indication to processing circuitry 210 of a biological impedance of the patient's tissue. In some examples, the sensing circuitry may detect if an electrode is not connected to the patient's tissue. For example, if the induced voltage is outside a threshold range, the electrodes may be disconnected from the body.

As shown in FIG. 2A, electrodes 244 and 240 may be separated and spaced at different locations relative to heart 212 and may sense electrocardiogram (ECG) signals as well as biological impedance signals from patient 208. Sensing electrodes 240, 242, 244 and 246 may also measure bioelectrical signals related to biological impedance, fluid-status monitoring, heart failure, sleep apnea, ischemia detection, lead connectivity detection (also referred to as lead off detection), as well as cardiac arrythmia such as atrial fibrillation (AF), ventricular tachycardia (VT), ventricular fibrillation (VF) and so on. In some examples, electrodes 240, 242, 244 and 246 may be located at other positions different than shown in FIG. 2A, e.g., lateral, or posterior relative to heart 212.

Figure 2B:
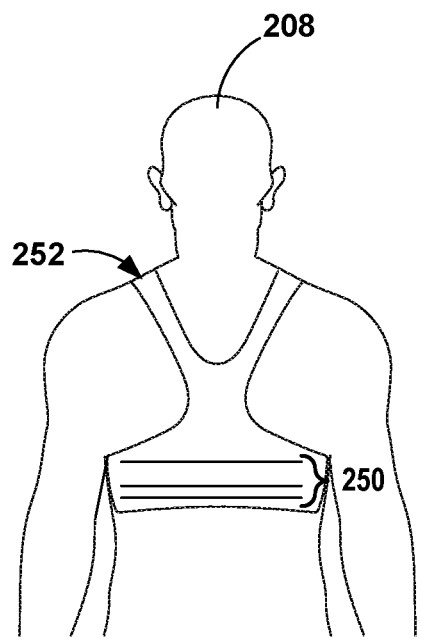
FIGS. 2B-2D are conceptual diagrams illustrating examples of a controllable apparatus configured to adjust the compression level of a wearable garment according to one or more techniques of this disclosure.
Figure 2C:
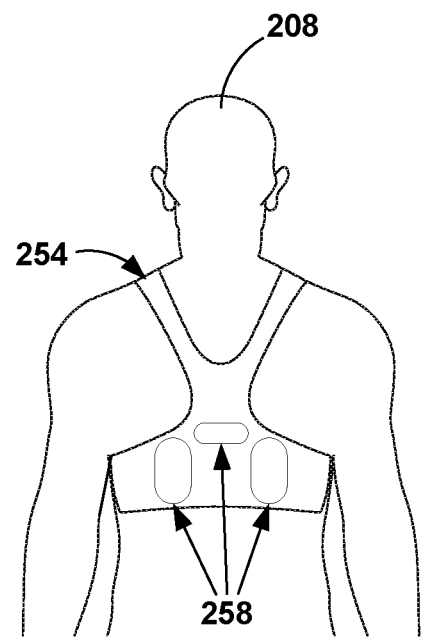
Figure 2D:
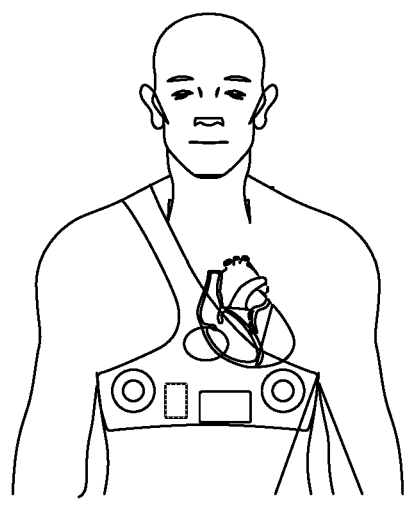
Figure 2D:
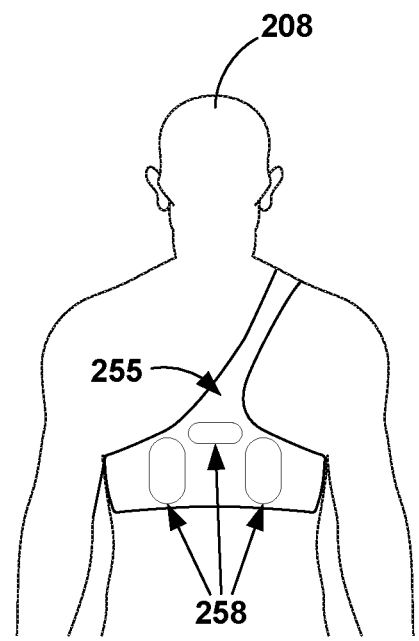

FIGS. 2B-2D are conceptual diagrams illustrating examples of a controllable apparatus configured to adjust the compression level of a wearable garment according to one or more techniques of this disclosure. Garments 252 and 254 are examples of garment 202 described above in relation to FIG. 2A and may have similar functions and characteristics.

In the example of FIG. 2B, garment 252 includes a controllable apparatus 250 that may change the compression level of garment 252. In some examples apparatus 250 may be implemented using a shape memory alloy (SMA), or similar material that when electrical current passes through conductors that include the shape memory alloy, the conductors may change shape, e.g., bend, expand or contract. One example shape memory alloy is nickel-titanium. In the example of FIG. 2B, processing circuitry 210, described above in relation to FIG. 2A, may control driver circuitry that may control current through apparatus 250 to adjust the compression level of garment 252. In some examples, apparatus 250 may include one or more mechanical sensors (not shown in FIG. 2B), such as a strain sensor, that may output an indication to processing circuitry 210 of the compression level of garment 252.

Similarly, in the example of FIG. 2C, garment 254 may include an apparatus, such as a controllable bladders 258 or similar mechanism, that may adjust the level of compression of garment 254. Processing circuitry may control one or more pumps and/or valves, that may adjust the volume of air, or other fluid, within bladders 258 to control the compression level of garment 254, similar to that described above in relation to FIGS. 2B and 2A. Garment 254 may also include one or more mechanical sensors, e.g., near bladders 258, (not shown in FIG. 2C) that may indicate to processing circuitry 210 the degree of compression for garment 254. In other examples, garment 254 may include other sensors, such as a sensor to determine pulsatility, e.g., similar to sensors in an automated blood pressure device.

FIG. 2D depicts a single shoulder version of wearable garment 255. The single shoulder wearable garment 255 may include any of the variations described above for FIGS. 2A-2C, including wearable bladders 258, SMA, or other controllable apparatus 250, mechanical sensors, and so on.

In some examples in which the garment comprises an WAED, processing circuitry 210 may cause the controllable apparatus to alert the patient that the WAED is preparing to deliver a defibrillation shock via the therapy electrodes described above in relation to FIG. 2A. In some examples, processing circuitry 210 may cause the apparatus to change between two or more compression levels rapidly, e.g., over a period of ten seconds or less. For example, processing circuitry 210 may cause the apparatus to compress between a tight compression level and a loose compression level three to five times over a period of less than ten seconds. This may warn the patient that the WAED has nearly completed charging and is ready to confirm a shockable arrythmia and deliver a defibrillation shock.

In other examples, processing circuitry 210 may also alert the patient using an audible alert (e.g., tone or voice) or a tactile alert (e.g., vibration mechanism) or both. By using a compressive or vibration alert, the WAED of this disclosure may provide a warning in situations in which patient 208 is hearing impaired or is in a noisy environment where an audible alert may be less effective.

Figure 3:
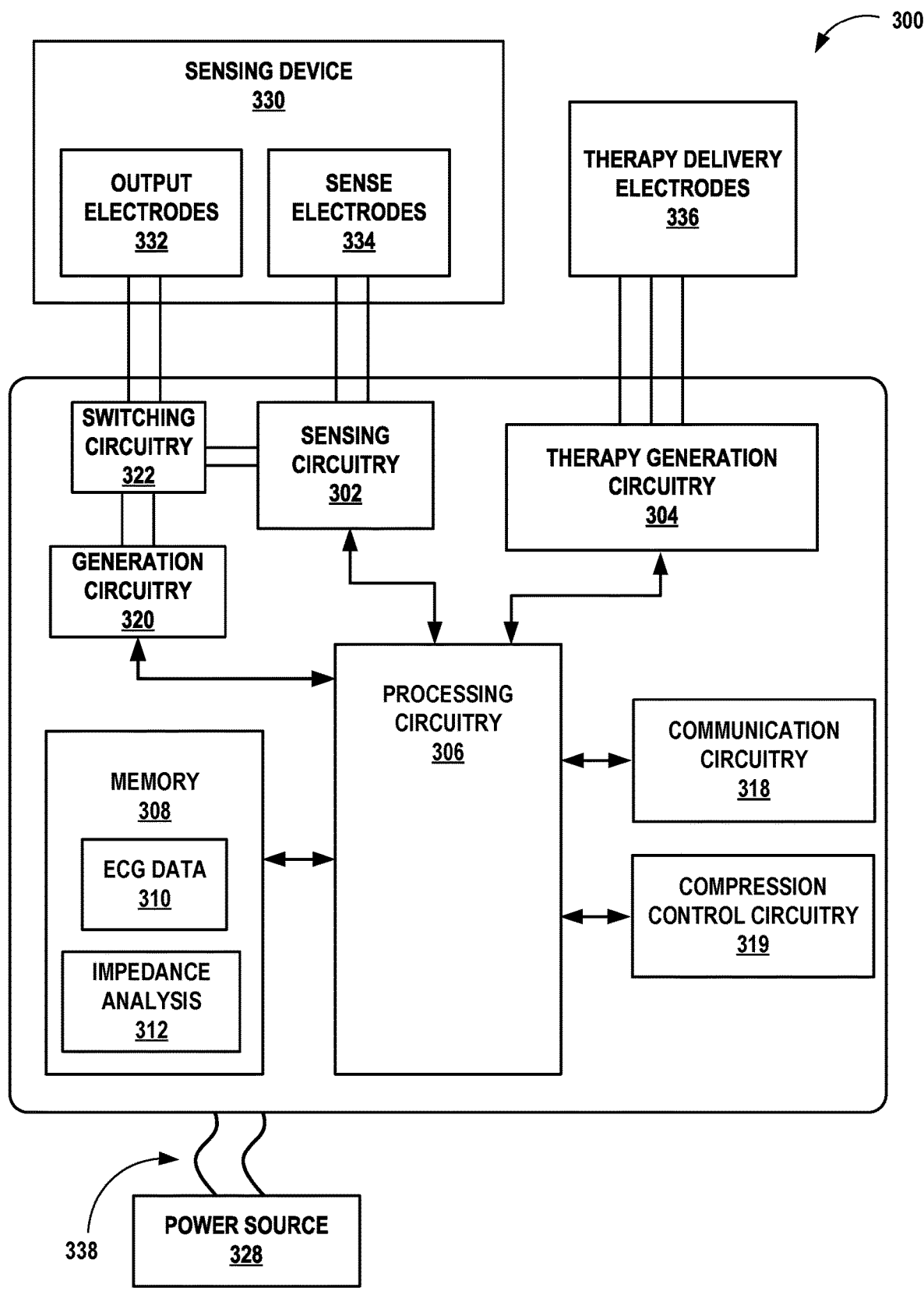
FIG. 3 is a functional block diagram of an example wearable medical device configured to monitor cardiac function and deliver electrical therapy.

FIG. 3 is a functional block diagram of an example wearable medical device configured to monitor cardiac function and deliver electrical therapy. WAED 300 of FIG. 3 is an example implementation of apparatus 110 described above in relation to FIG. 1 and any of the garments described above in relation to FIGS. 2A-2D. In the example illustrated by FIG. 3, WAED 300 includes sensing circuitry 302 connected to sensing device 330, generation circuitry 320, switching circuitry 322, therapy generation circuitry 304 connected to therapy delivery electrodes 336, processing circuitry 306, memory 308, and communication circuitry 318. WAED 300 may receive power from power source 328 via connection 338.

Processing circuitry 306 and memory 308 are respectively examples of processing circuitry 210 and the associated memory described above in relation to FIG. 2A and have similar functions and characteristics. For example, memory 308 may store program instructions, including one or more program modules, which are executable by processing circuitry 306. When executed by processing circuitry 306, such program instructions may cause processing circuitry 306 and WAED 300 to provide the functionality described herein.

As described above in relation to FIG. 2A, sensing circuitry 302 may be configured to receive bioelectrical signals from sense electrodes 334, such as biological impedance measurements and/or electrocardiogram (ECG) signals from a patient, such as patient 210. In some examples, sensing circuitry 302 is configured to sense cardiac events within the ECG signals based on the depolarization of myocardial tissue, e.g., P-waves and R-waves. Sensing circuitry 302 may include a switching circuitry 322 for selectively coupling output electrodes 332 to sensing circuitry 302 to monitor the bioelectrical signals. Switching circuitry 322 may include a switch array, switch matrix, multiplexer, or any other type of switching device suitable to selectively couple one or more of electrodes 332 to sensing circuitry 302. In other examples, switching circuitry 322 may configure the electrodes to reverse the polarity of the signals, as well as to provide calibration functions.

Sensing circuitry 302 may include multiple sensing channels. Each sensing channel may be configured to amplify, filter, and rectify the bioelectrical signal received from selected electrodes coupled to the respective sensing channel to detect cardiac events, e.g., P-waves and/or R-waves, or ventricular fibrillation (VF) or ventricular tachycardiac (VT) signals, biological impedance, or other signals, as described above in relation to FIG. 2A. Sensing circuitry 302 may include cardiac event detection circuitry that detects a cardiac event when the cardiac electrical signal crosses a sensing threshold. Sensing circuitry 302 may include a rectifier, filter and/or amplifier, a sense amplifier, comparator, and/or analog-to-digital converter.

Generation circuitry 320 may output the impedance measurement signal, for example via output electrodes 332. Output electrodes 332 may be an example of electrodes 246 and 242 described above in relation to FIG. 2A. In some examples, the impedance measurement signal may travel between output electrodes 332 through the patient's body tissue. For example, the impedance measurement signal may be a constant current signal that passes between output electrodes 332 (e.g., electrodes 246 and 242). The impedance measurement signal may measure an induced voltage during the delivery of the current signal via sense electrodes 334. Sense electrodes 334 may be an example of sensing electrodes 240 and 244 described above in relation to FIG. 2A. In other words, in some examples, sensing device 330 may provide a four-wire impedance measurement to processing circuitry 306. In some examples, processing circuitry 306 may initiate an impedance measurement periodically and/or in response to an event. For example, processing circuitry 306 may initiate any of several types of biological impedance measurements one, two or more predetermined times per day. Processing circuitry may also initiate a measurement in response to a cardiac event, a predetermined movement or activity, a change in compression level, and so on. Some examples of types of biological impedance measurements may include body fluid level measurement (e.g., for kidney failure patient continuous monitoring or during dialysis), heart failure patient monitoring (as body fluid accumulated), sleep apnea (respiration monitor), body mass index (BMI) measurement, and so on. Processing circuitry 306 may cause generation circuitry 320 to adjust an output amplitude, frequency, pulse width or other characteristics of an output signal, for example, depending on the type of biological impedance measurement. In some examples, one or more electrodes may be used as part of common mode noise rejection circuitry.

In some examples, sensing circuitry 302 may include other types of sensors including accelerometers, temperature sensors, pressure sensors. In some examples, sensing circuitry 302 may communicate with other remote sensors implanted in, worn on or placed near patient 208, described above in relation to FIGS. 1 and 2A (not shown in FIG. 3) via communication circuitry 318. In some examples, other remote sensors may communicate directly with processing circuitry 306 via communication circuitry 318. In some examples the other types of sensors, may provide information such as patient posture, movement, activity, and other information.

Sensing circuitry 302 may output an indication to processing circuitry 306 in response to sensing of a cardiac event (e.g., detected P-waves or R-waves). In this manner, processing circuitry 306 may receive detected cardiac event signals corresponding to the occurrence of detected R-waves or P-waves. Indications of detected R-waves and P-waves may be used for detecting ventricular and/or atrial tachyarrhythmia episodes, e.g., ventricular, or atrial fibrillation episodes. Sensing circuitry 302 may also pass one or more digitized ECG signals to processing circuitry 306 for analysis, e.g., for use in cardiac rhythm discrimination. Processing circuitry 306 may use the indications of R-waves and/or the digitized ventricular ECG signals to detect diagnostic events and potential sensing issues, according to the techniques described herein. Indications of R-wave and P-wave timing, as well as digitized ECGs, may be stored in memory 308 as ECG data 310. In some examples, analysis of the digitized ECG signals may include morphology (shape) analysis, such as ECG template matching and other types of ECG morphology analysis.

Memory 308 may also store an impedance analysis module 312. Impedance analysis module 312 may be a software, firmware, or combination module executable by processing circuitry 306 to cause processing circuitry 306 to provide functionality related to identifying sensing issues, such as a lead off or other lead disconnection issues and sensing biological impedance. Functionality related to identifying sensing issues may include providing an alert, and/or modifying sensing or therapy provided by WAED 300. As described above in relation to FIG. 2A, biological impedance measurements may provide information regarding fluid-status monitoring, heart failure, sleep apnea, and ischemia detection, connectivity detection as examples.

Processing circuitry 306 may control therapy generation circuitry 304 to deliver electrical therapy, e.g., cardioversion or defibrillation shock pulses, to heart 212 (depicted in FIG. 2A) according to therapy parameters stored in memory 308. In the example of FIG. 3, therapy generation circuitry 304 is electrically coupled to therapy electrodes 336. Therapy delivery electrodes 336 is an example of therapy delivery electrodes 230, 232 and 234 described above in relation to FIG. 2A.

Therapy delivery circuit 304 may include charging circuitry, one or more charge storage devices, such as one or more high voltage capacitors and/or one or more low voltage capacitors and switching circuitry (not shown in FIG. 3) that controls when the capacitor(s) are discharged to selected combinations of therapy delivery electrodes 336. Therapy delivery circuit 304 may control charging of capacitors to a programmed pulse amplitude and discharging of the capacitors for a programmed pulse width according to control signals received from processing circuitry 306.

In some examples, communication circuitry 318 is used to communicate with an external device, for transmitting data accumulated by WAED 300 and for receiving interrogation and programming commands from external devices 130, described above in relation to FIG. 1. Under the control of processing circuitry 306, communication circuitry 318 may transmit an alert to notify a clinician and/or the patient that WAED 300 has detected a possible sensing issue with the atrial and/or ventricular leads. This alert enables the clinician to perform additional testing to confirm the issue and to intervene, if necessary, to replace the lead, fix the connection, reposition the lead, or to prevent unnecessary defibrillation therapy from being delivered to the patient. In other embodiments, WAED 300 may be equipped with alert circuitry configured to emit a sensory alert perceptible by the patient, e.g., a vibration, compressive or an audible tone, under the control of processing circuitry 306 to alert the patient to the possibility of a possible sensing issue, impeding defibrillation shock and so on, as described above in relation to FIGS. 2B and 2C.

Processing circuitry 306 may adjust the compression level of the garment via compression control circuitry 319. Compression control circuitry 319 may include driver circuits, logic circuitry or other processing circuitry, and other components to control the compression level of a wearable garment according to one or more techniques of this disclosure, such as garment2 202, 252 and 254 described above in relation to FIGS. 2A-2C. In some examples, compression control circuitry 319 may include circuitry configured to pass electrical current through the shape memory alloy of garment 252. In other examples, compression control circuitry 319 may include circuitry to control the bladders, or other devices of garment 254.

In some examples, compression control circuitry 319 may include feedback circuitry to receive signals from the one or more mechanical sensors (not shown in FIG. 3) that provide an indication of the compression level of the garment. In other examples, processing circuitry 306 may receive the signals from the mechanical sensors and cause compression control circuitry 319 to adjust the compression level of the garment.

In some examples, processing circuitry 306 may send commands to compression control circuitry 319 to cause the compression level to rapidly change between two or more compression levels, for example, to alert the patient. In other examples, processing circuitry 306 may send an alert command to compression control circuitry 319, and compression control circuitry 319 may manage the different compression levels as well as the timing between compression levels. In some examples, though shown as a separate block in the example of FIG. 3, compression control circuitry 319 may be embedded as part of processing circuitry 306.

Figure 4:
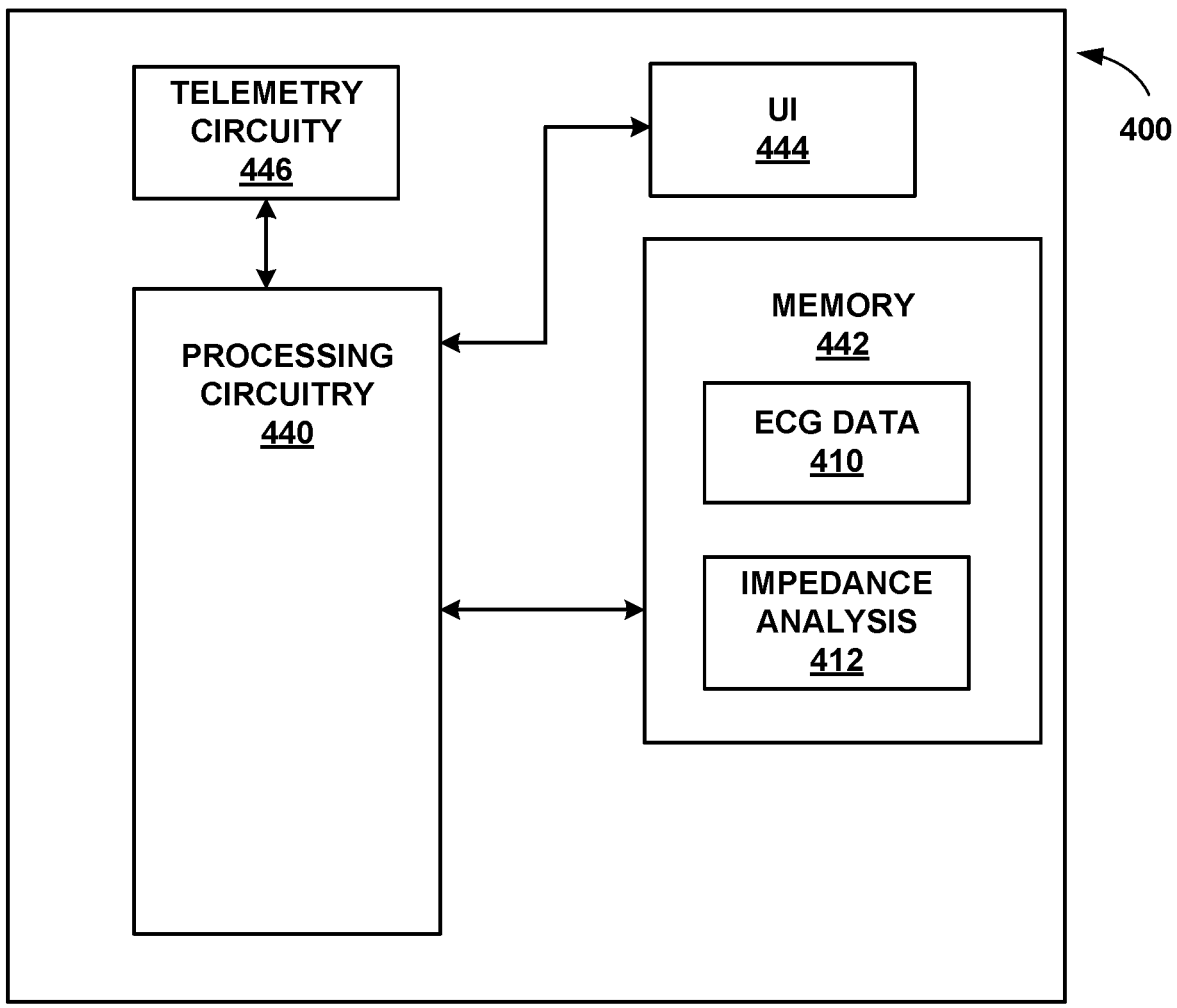
FIG. 4 is a functional block diagram of an external device configured to communicate with a wearable medical device.

FIG. 4 is a functional block diagram of an external device configured to communicate with a wearable medical device. External device 400 depicted in FIG. 4 is an example of external devices 170 described above in relation to FIG. 1. In the example of FIG. 4, external device 400 includes processing circuitry 440, memory 442, user interface (UI) 444, and telemetry circuitry 446. External device 400 may be a dedicated hardware device with dedicated software for the programming and/or interrogation of the wearable medical device. Alternatively, external device 400 may be an off-the-shelf computing device, which may execute an application that enables external device 400 to program and/or interrogate the wearable medical device. In some examples, external device 400 may be a portable computing device, such as portable device 228 as well as a wearable device, such as devices 222 and 226, described above in relation to FIG. 2A. In other examples, the functionality ascribed to external device 400 may also be implemented in medical devices worn by or implanted in patient 208 (not shown in FIG. 3B), such as an infusion pump for drug delivery, a leadless pacemaker, or other types of medical devices.

In some examples, a user may use external device 400 to select or program values for operational parameters of the wearable medical device, e.g., for cardiac sensing, therapy delivery, to configure the type of alert, e.g., audible, compressive, vibration, and other parameters. In some examples, a user may use external device 400 to receive data collected by the wearable medical device, such as cardiac ECG data 410 or other operational and performance data of the wearable medical device. The user may also receive one or more alerts provided by the wearable medical device. The user may interact with external device 400 via UI 444, which may include a display to present a graphical user interface to a user, and a keypad or another mechanism for receiving input from a user. External device 400 may communicate wirelessly with the wearable medical device using telemetry circuitry 446, which may be configured for RF communication, including inductive communication, with communication circuitry 318 of WAED 300 depicted in FIG. 3. In other examples, external device 400 may also communicate via a wired connection, such as via universal serial bus (USB), ethernet, or some other wired connection.

Similar to processing circuitry 306 described above in relation to FIG. 3, processing circuitry 440 may include any combination of integrated circuitry, discrete logic circuitry, analog circuitry, such as one or more microprocessors, DSPs, ASICs, or FPGAs. In some examples, processing circuitry 440 may be configured with more processing power than the processing power available to processing circuitry 106. Processing circuitry 440 may be configured to perform more complex calculations and analysis functions than performed by the processing circuitry in the wearable medical device.

As with memory 308, described above in relation to FIG. 3, memory 442 may store program instructions, which may include one or more program modules and are executable by processing circuitry 440. When executed by processing circuitry 440, such program instructions may cause processing circuitry 440 and external device 400 to provide the functionality described herein. The program instructions may be embodied in software, firmware, or other volatile, non-volatile, magnetic, optical, or electrical media, such as a RAM, ROM, NVRAM, EEPROM, flash memory, or any other digital media.

In some examples, processing circuitry 440 of external device 400 may be configured to provide some or all of the functionality ascribed to processing circuitry 306 of the wearable medical device. For example, processing circuitry 440 may receive ECG data 410 from the wearable medical device via telemetry circuitry 446, e.g., sensed via sensing device lead 330 depicted in FIG. 3, and may store the ECG data 410 in memory 442. ECG data 410 may be current ECG data, or data previously collected and stored by the wearable medical device. Using ECG data 410, processing circuitry 440 of external device 400 may identify characteristics of the atrial and ventricular EGM(s) indicative of possible sensing issues with WAED 300 described above in relation to FIG. 3, including sensed noise, biological impedance trends and so on. Based on the detection of possible sensing issues, or other diagnostic events, processing circuitry 440 may provide an alert to a user, e.g., via UI 444. In some examples, impedance analysis module 412 may provide the functionality for the detection of possible sensing issues as well as biological impedance that may be used to monitor the patient.

Figure 5:
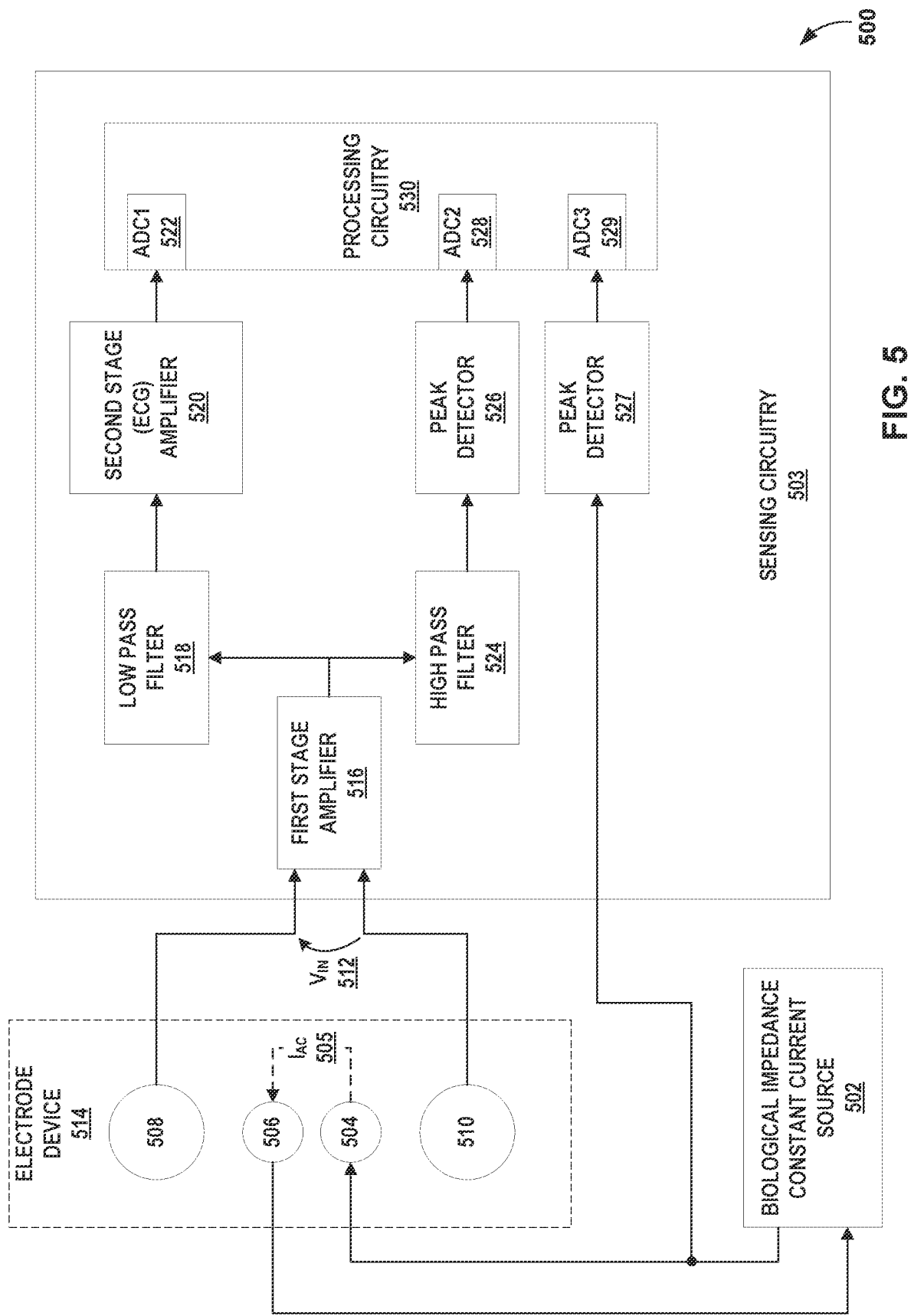
FIG. 5 is a block diagram illustrating a system including an electrode device configured to sense bioelectrical signals from a patient according to one or more techniques of this disclosure.

FIG. 5 is a block diagram illustrating a system including an electrode device configured to sense bioelectrical signals from a patient according to one or more techniques of this disclosure. System 500 is an example of circuitry that may be included in the garments and WAED 300 described above in relation to FIGS. 2A-2D and 3. In the example of FIG. 5, system 500 includes sensing circuitry 503, electrode device 514 and current source 502.

Electrode device 514 includes output electrodes 504 and 506 arranged in an area between voltage sensing electrodes 508 and 510. In other words, electrode 508 and electrode 510 define an area between electrodes 508 and 510. Electrodes 504 and 506 are located in the area between electrodes 508 and 510. In other examples, the arrangement of sensing electrodes 240, 242, 244 and 246 described above in relation to FIG. 2A is also an example of electrode device 514.

Output electrodes 504 and 506 receive an impedance measurement signal, Iac 505, e.g., from current source 502. In the example of system 500, current source 502 may be configured to output impedance measurement signal Iac 505 as a constant current magnitude signal, i.e., a fixed current amplitude. In some examples, Iac 505 may be an alternating current (AC) signal, e.g., with a constant current peak-to-peak amplitude.

In some examples, electrodes 508 and 510 may be configured to measure the biological impedance between electrodes 508 and 510 based on impedance measurement signal Iac 505. In other words, electrode device 514 may be configured to provide a four-wire impedance measurement to processing circuitry 530, via first stage amplifier 516, as described above in relation to FIG. 3. Processing circuitry 530 may determine the biological impedance according to the following equation:

$$Z_{biological} = \frac{V_{in}}{I_{AC}}.$$

In other examples, processing circuitry 530 may be configured to determine an ECG signal based on Vin 512, as measured by electrodes 508 and 510.

In other examples, processing circuitry 530 may be configured to determine an ECG signal based on $V_{in}$ 512, as measured by electrodes 508 and 510. Sensing circuitry 503 may be an example of sensing circuitry 302 described above in relation to FIG. 3 and may include the same functions and characteristics. Sensing circuitry may include a first sensing path including low pass filter 518 and second stage amplifier 520. Second stage amplifier 520 may also be referred to as ECG amplifier 520. Second stage amplifier 520 may output the amplified and filtered voltage signal, Vin 612 to analog-to-digital converter ADC1 522. In some examples, system 500 may measure ECG and impedance simultaneously. For example, amplifier 516 may amplify both the ECG signal AND the impedance signals. The techniques of this disclosure may provide advantages over other types of measurement circuits. For example, a circuit arrangement like that depicted by system 500, as well as system 300 described above in relation to FIG. 3, simplify the measurement circuitry, such by eliminating one or more multiplexer (MUX) circuits, and amplifier circuits.

Sensing circuitry 503 may include a second sensing path including high pass filter 524, peak detector 526 and ADC2 528. In some examples, high pass filter 524 may be implemented by a capacitor. In some examples, peak detector 526 may include a diode and be configured to detect negative peaks from first state amplifier 516.

In other examples, system 500 may include a second peak detector 527 coupled to ADC3 529. ADC3 529 may receive the output of peak detector 527 and provide a digitized version to processing circuitry 530. Including peak detector 527 may provide a different two-point measurement of the impedance, which may provide processing circuit 530 information to detect electrode-tissue interface issues, such as intermittent contact or an open circuit. In other words, the current is injected to electrode 504 and return from electrode 506. Peak detector 527 may detect either electrode is not connected to body. The sensing electrodes 510 and 508, which correlate to electrodes 240 and 244 depicted in FIG. 2A, may measure the induced voltage in the patient's tissue. If the voltage is outside a threshold range, processing circuitry 530 may determine that the electrodes may be disconnected from the body.

As shown in the example of FIG. 5, ADC1 522, ADC2 528 and ADC3 529 may be part of processing circuitry 530. In other examples, ADC1 522, ADC2 528 and ADC3 529 may be separate circuitry that is operatively connected to processing circuitry 530. In some examples, the measured biological impedance may be recorded and reviewed for trends, e.g., trends in BMI, body fluid levels and so on. In other examples, the measured biological impedance may be compared to a threshold and used to provide patient or caregiver notification and/or cause processing circuitry 530 to perform some action. For example, breathing during sleep may be compared to a threshold to trigger a notification of potential sleep apnea. In other examples, when the induced voltage amplitude is higher than a threshold, processing circuitry 530 may determine that an electrode may be disconnected.

Figure 6A:
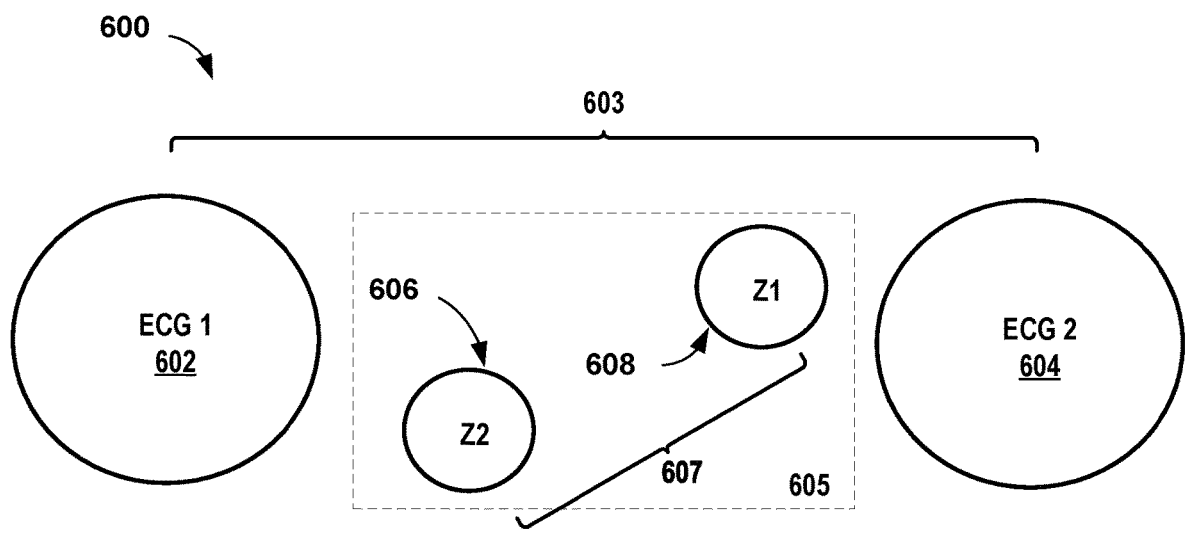
FIGS. 6A-6D are examples implementations of the electrode device according to one or more techniques of this disclosure.
Figure 6B:
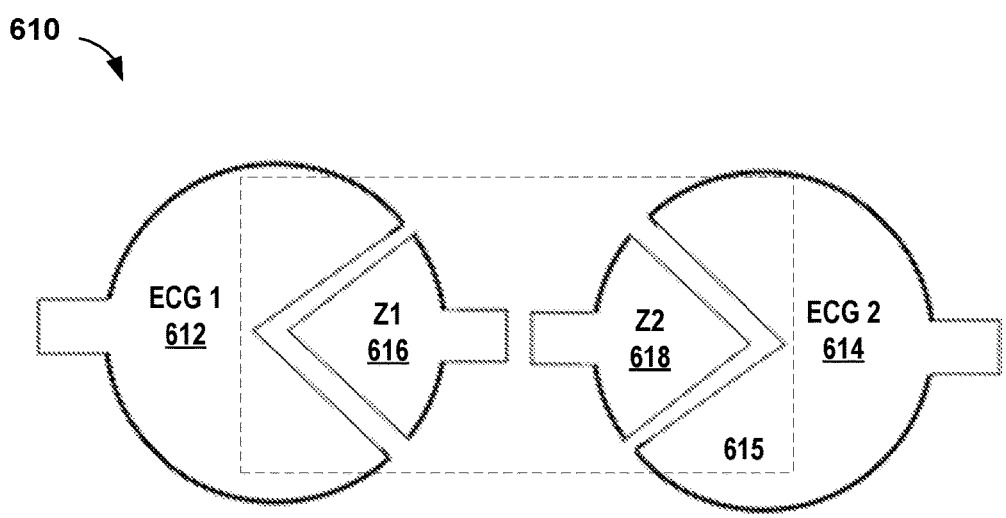
Figure 6C:
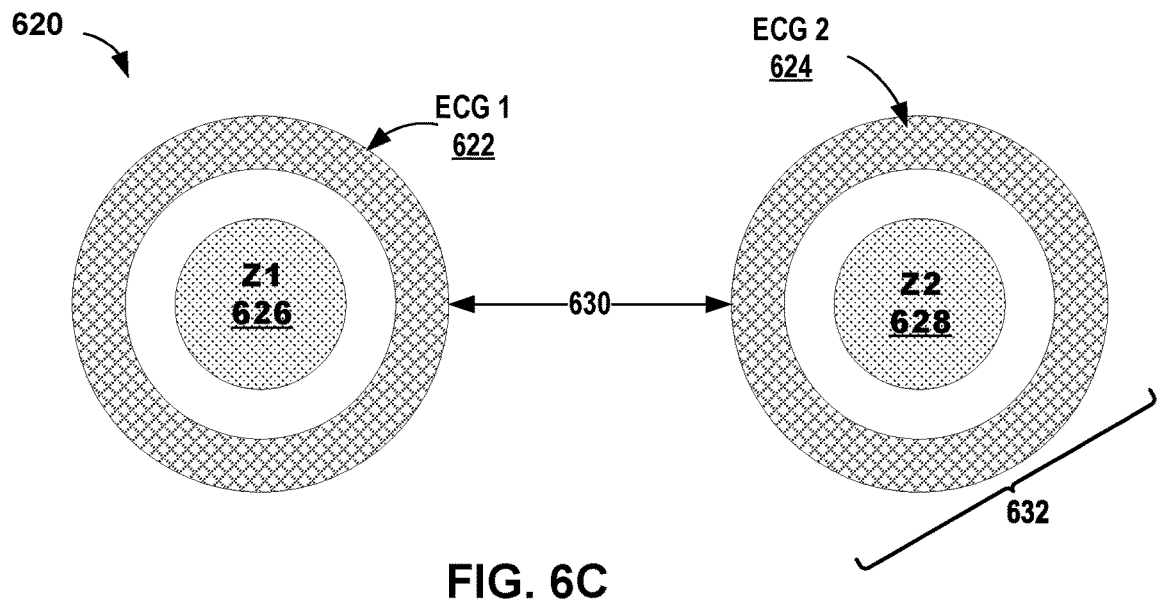

FIGS. 6A-6C are examples implementations of the electrode device according to one or more techniques of this disclosure. Electrode devices 600, 610 and 630 are examples of sensing device 330 and electrode device 514 described above in relation to FIGS. 3 and 5, respectively.

Electrode device 600, in the example of FIG. 6A, is arranged similar to electrode device 514, depicted in FIG. 5. Electrodes ECG1 602 and ECG2 604 define an area 605 between electrodes ECG 602 and ECG2 604. Electrodes Z2 606 and Z1 608 are located in area 605 between electrodes ECG1 602 and ECG2 604. Also, a first distance 607 between electrode Z2 606 and electrode and Z1 608 is smaller than a second distance 603 between electrode ECG1 602 and electrode ECG2 604.

The geometric shape of electrodes ECG1 602 ECG2 604 define a substantially circular disk with a diameter of a first dimension. In some examples the first dimension may be 20 millimeters (mm), 30 mm, 50 mm, or some other diameter. The geometric shape of electrodes Z2 606 and Z1 608 in the example of FIG. 6A also define a substantially circular disk with a diameter that is less than the diameter of electrodes ECG1 602 and ECG2 604. In other examples, the geometric shape of the electrodes may be an oval, octagon, square, rectangle, or any other geometric shape. The dimensions for electrode ECG1 602 may be approximately the same as for electrode ECG2 604 in some examples. Similarly, in some examples, the dimensions for electrode Z2 606 may be approximately the same as for electrode Z1 608.

Selecting the electrode size and shape may depend on a particular application, patient comfort and other factors. A larger size electrode may have better contact to the body but may take up more space. For ECG signals, larger electrode size may increase signal to noise ratio when compared to a smaller electrode. However, an electrode that is too large may make the electrode location less specific. Also, larger distance between the ECG electrodes may result higher signal amplitude.

Similar to electrode device 600, in the example of FIG. 6B, electrode device 610 may include electrodes ECG1 612 and ECG2 602 define an area 615 between electrodes ECG 1 612 and ECG2 614. Electrodes Z2 616 and Z1 618 are located in area 615 between electrodes ECG1 612 and ECG2 614. Also, as described above in relation to FIG. 6A, a first distance between electrode Z2 616 electrode and Z1 618 is smaller than a second distance between electrode ECG1 612 and electrode ECG2 614.

The geometric shape of electrodes ECG1 612 and ECG2 614 define a substantially circular disk with a triangular or pie-shaped portion removed. Electrode Z1 616, in the example of FIG. 6B, defines a triangular or pie-shape located in the removed portion of electrode ECG1 612. Similarly, electrode Z1 616, in the example of FIG. 6B, defines a triangular or pie-shape located in the removed portion of electrode ECG1 612.

Also, as with the electrodes shown in any of FIGS. 6A-6C, the geometric shape of the ECG1 and ECG2 electrodes form a first surface area in contact with the patient's skin and the geometric shape of the Z1 and Z2 electrodes form a second surface area in contact with the patient's skin. In the examples of FIGS. 6A-6C, the first surface area may be the same as or larger than the second surface area. In some examples, the first surface area may be two to four times larger than the second surface area.

In the example of FIG. 6C, electrode ECG1 622 and Z1 626 form a concentric arrangement. Electrode Z1 626 defines a substantially circular disk-shaped electrode, while electrode ECG1 622 defines a substantially circular ring shaped electrode surrounding electrode Z1 626. Similarly, electrode ECG2 624 and Z2 628 form a concentric arrangement. Electrode Z2 628 defines a substantially circular disk shaped electrode, while electrode ECG2 624 defines a substantially circular ring-shaped electrode surrounding electrode Z2 628. As described above in relation to FIG. 6A, in other examples, the geometric shape of the electrodes may be implemented an oval, octagon, square, rectangle or any other geometric shape. The dimensions for electrode ECG1 622 may be approximately the same as for electrode ECG2 624 in some examples. Similarly, in some examples, the dimensions for electrode Z2 626 may be approximately the same as for electrode Z1 628. As noted above, the distance 630 between the electrodes may impact the signal amplitude for some bioelectrical signals. In some examples, the distance 630 may be many times the diameter 632 of electrodes ECG1 622 and ECG2 624. FIG. 6C is an example and may not be to scale.

Figure 6D:
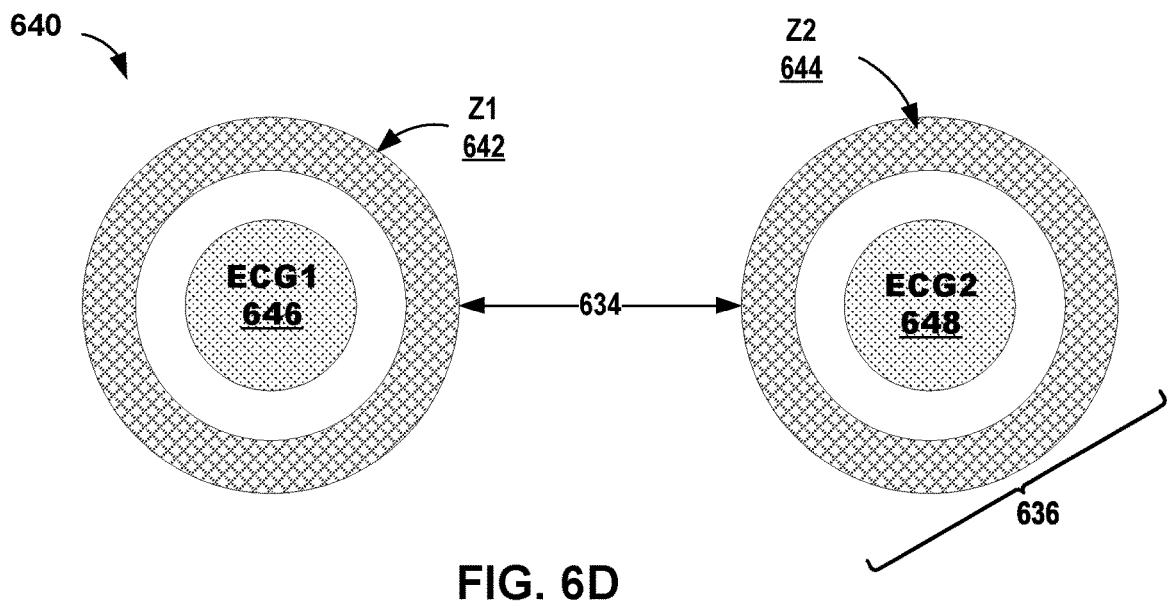

Similar to FIG. 6C, in the example of FIG. 6D, each pair of electrode ECG1 622 and Z1 626 and electrode ECG2 624 and Z2 628 form a concentric arrangement. In FIG. 6D, the locations of the output electrodes and the voltage sensing electrodes have been reversed, when compared to FIG. 6C. Electrode ECG1 646 defines a substantially circular disk-shaped electrode, while electrode Z1 642 defines a substantially circular ring shaped electrode surrounding electrode ECG1 646. Electrode ECG2 648 defines a substantially circular disk shaped electrode, while electrode Z2 644 defines a substantially circular ring-shaped electrode surrounding electrode ECG2 648. As with FIG. 6C, the distance 634 between the electrodes may be many times the diameter 636. Also, the area of electrode ECG1 622 in FIG. 6C may be approximately the same as for electrode Z1 642 in FIG. 6D. Similarly, in some examples, the dimensions for ECG2 electrode 624 may be approximately the same as for electrode Z2 646.

Figure 7:
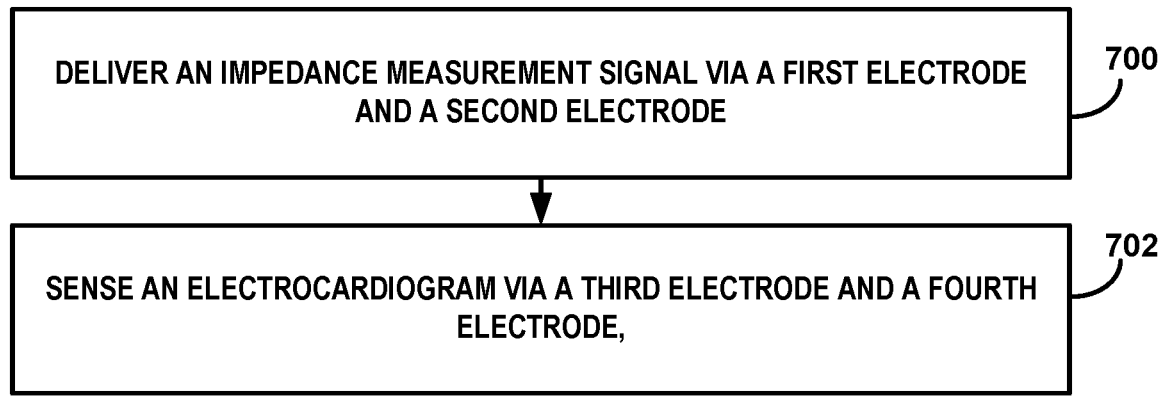
FIG. 7 is a flow diagram illustrating an example operation of the electrode device according to one or more techniques of this disclosure.

FIG. 7 is a flowchart illustrating an example operation of the electrode device according to one or more techniques of this disclosure. The operation of FIG. 7 will be described in terms of FIG. 6C for convenience.

A medical device, such as WAED 300, arranged as shown by garment 202, described above in relation to FIGS. 3 and 2 respectively, may include circuitry configured to deliver an impedance measurement signal via a first electrode, e.g., electrode Z1 626 and a second electrode, e.g., electrode Z2 628 (700). The impedance measurement signal may travel through tissue of a patient, as described above in relation to FIG. 5. In some examples, electrode ECG1 622 along with electrode ECG2 624, may measure a voltage which develops in the area between electrodes ECG1 622 and electrode ECG2 624 based on the impedance measurement signal. In other words, electrode device 620 may provide a four-wire impedance measurement to processing circuitry of the medical device. For example, signal generation circuitry 320 may be configured to output the impedance measurement signal, such as a constant current signal at a first time for a predetermined duration. Sensing circuitry 302 may be further configured to measure a biological impedance via sensing device 330 during the predetermined duration and based on the output constant current signal.

Also, the medical device, may sense an electrocardiogram from the patient via electrode ECG1 622 and electrode ECG2 624 based on a voltage measured between electrode ECG1 622 and electrode ECG2 624 (702). The measured voltage may be caused by cardiac activity, such as depolarization of heart tissue. As described above in relation to FIG. 2A, each of ECG1 622, electrode ECG2 624, electrode Z2 626 and electrode Z1 628 may be configured to be placed in contact with skin of the patient and held in position with a compressive member, e.g., garment 202. The electrodes may be free of adhesives, which may improve long term patient comfort, as described above in relation to FIGS. 2A-2D.

Figure 8:
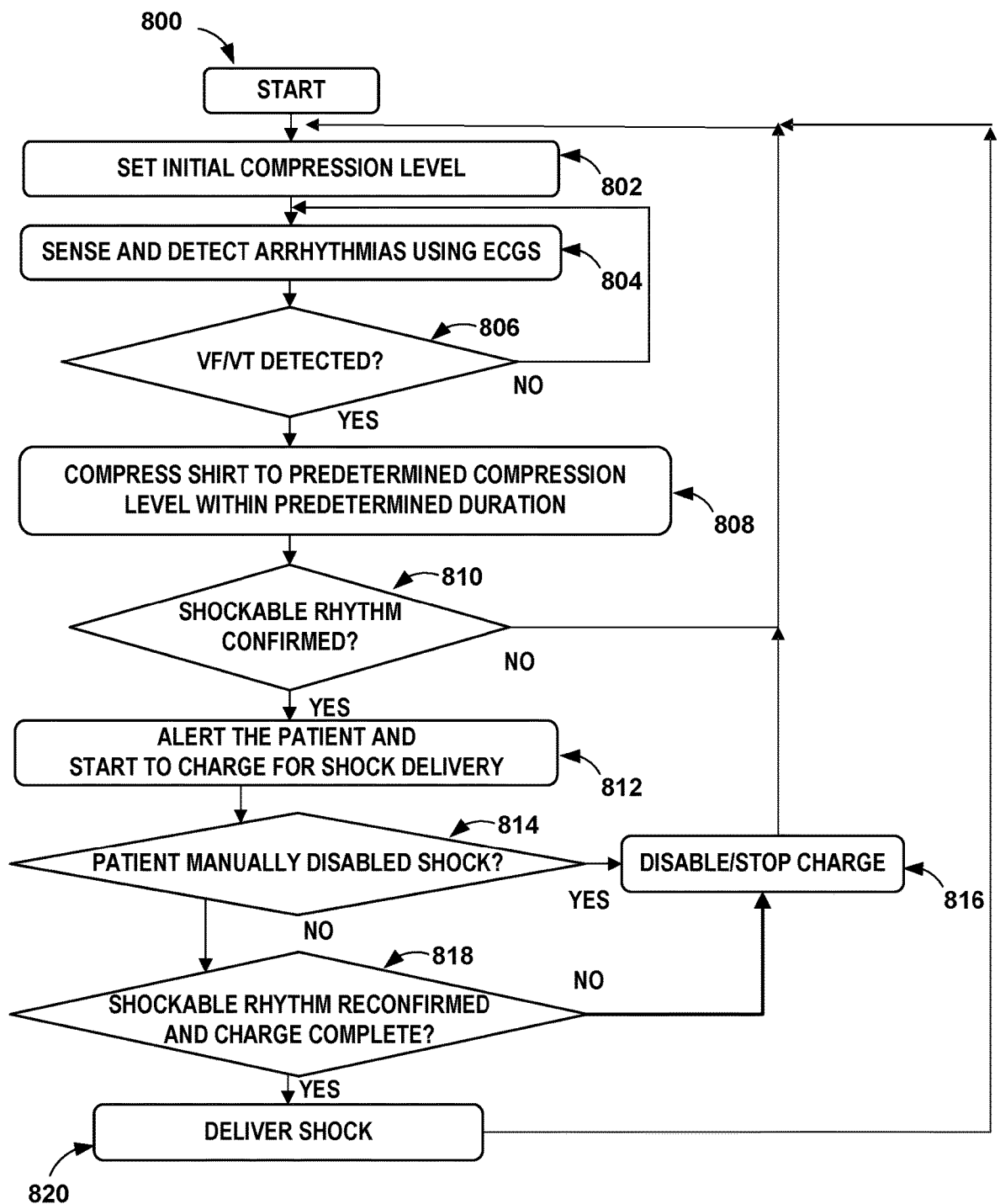
FIG. 8 is a flow diagram illustrating an example operation of the wearable garment, which includes a medical device, according to one or more techniques of this disclosure.

FIG. 8 is a flow diagram illustrating an example operation of the wearable garment, which includes a medical device, according to one or more techniques of this disclosure. The flow diagram of FIG. 8 may be described in terms of FIGS. 2A and 3, unless otherwise noted.

In the example of FIG. 8, processing circuitry 210 of garment 202 may start (800) by receiving an indication from a mechanical sensor, e.g., a strain sensor, or similar mechanical sensor that a patient has put on garment 202. The processing circuitry may determine a compression level for garment 202, based on the received indication, which may be affected by the size of garment 202 and height, weight and so on of patient 208.

Processing circuitry 210 of the medical device may set the compression level for the garment to an initial compression level at a first time (802). In some examples, compression control circuitry 319 may set the initial compression level to prioritize patient comfort over receiving noise-free bioelectrical signals via the electrodes of sensing device 330. In other examples, compression control circuitry 319 may set a tighter compression level to establish a baseline signal level for the bioelectrical signals from the skin of patient 208, then relax the compression level to prioritize patient comfort. In any case, the compression level of garment 202 may locate the electrodes on the patient's skin such that the plurality of electrodes receives bioelectrical signals from a patient.

At a later time, the processing circuitry may cause compression control circuitry 319 to change the compression level from the initial level to a second compression level based on, for example, one or more of the indication of the compression level from the mechanical sensor and the received bioelectrical signals. In some examples processing circuitry 210 may sense and detect a cardiac arrhythmia using ECGs via the electrodes of sensing device 330 (804). Processing circuitry 210 determines whether the detected cardiac arrhythmia is a suspected shockable cardiac arrhythmia, e.g., ventricular tachycardia (VT) or ventricular fibrillation (VF) (806). When the processing circuitry 210 determines that the detected cardiac arrhythmia is not a suspected shockable cardiac arrythmia, such as a supraventricular tachycardia (SVT), atrial fibrillation, or other non-shockable rhythm (NO branch of 806), processing circuitry continues to monitor for a cardiac arrhythmia.

In other examples, processing circuitry 210 may detect that the cardiac arrythmia is a suspected shockable cardiac arrhythmia (YES branch of 806), and processing circuitry 210 may cause the compression level to change to a tighter compression level, which may press the electrodes more tightly against the skin of patient 208 (808). In some examples, pressing the electrodes more tightly to the skin may reduce skin-to-electrode movement, and increase the surface area of skin in contact with the electrode. In this manner the tighter compression level may provide a stronger (e.g., higher amplitude ECG) bioelectrical signal that may have less noise. In some examples, processing circuitry 210 may cause the compression level to change to a tighter level within a predetermined duration, e.g., within five seconds, three seconds, ten seconds, or some other duration (808). In some examples, processing circuitry 210 may retrieve from a memory one or more predetermined target compression levels, e.g., based on patient activity, posture, detected arrhythmia, patient comfort and so on. Processing circuitry may control the adjustment of the compression level of garment 202 to match a selected target compression level, e.g., within a threshold amount of compression as measured by the mechanical sensor.

While at the tighter compression level, processing circuitry 210 may confirm whether the cardiac arrhythmia is treatable by a defibrillation shock. In the example, of a short term VT episode, e.g., VT lasting for a few seconds, processing circuitry 210 may not be able to confirm the shockable rhythm (NO branch of 810). In the example of an arrhythmia such as VT or VF, the arrhythmia may be treatable by a defibrillation shock (YES branch of 810).

In response to confirming that the cardiac arrhythmia is treatable by the defibrillation shock, processing circuitry 210 may alert patient 208 that the medical device will deliver the defibrillation shock based on the confirmation (812). As described above in relation to FIG. 2A, the medical device may output a vibration, audio signal, or may change compression levels in a manner that alerts the patient. In some examples, therapy generation circuitry 304 may begin charging an electrical energy storage device, e.g., one or more capacitors, to prepare for defibrillation shock delivery (812).

In some examples, garment 202 may include a button, switch, or some other input device e.g., a microphone for a voice command, configured to allow patient 208 to manually pause or disable delivery of the defibrillation shock. In other examples, the patient may provide the indication to disable the shock using any one of external devices 170, wearable devices 222 and 226 and a portable computing device 228 described above in relation to FIGS. 1 and 2. For example, if the patient is driving, pausing the shock delivery may allow the patient to stop in a safe location. In response to receiving an input from patient 208 to disable the shock (YES branch of 814), processing circuitry may cause the medical device to stop charging and disable delivery of the defibrillation shock (816).

In other examples, patient 208 may not disable the shock (NO branch of 814). Once the charging is complete, processing circuitry 210 may reconfirm that processing circuitry 210 is still receiving an indication of a shockable arrythmia via sensing device 330 (YES branch of 818). In response, the processing circuitry may cause the therapy delivery circuitry, e.g., therapy generation circuitry 304 and therapy delivery electrodes 336 of the medical device to deliver the defibrillation shock (820).

In other examples, the arrhythmia may have ended on its own, or the indication of the arrhythmia may have been caused by noise or some other issue. Processing circuitry 210 may not be able to reconfirm the shockable rhythm (NO branch of 818) and stop charging (816).

Figure 9:
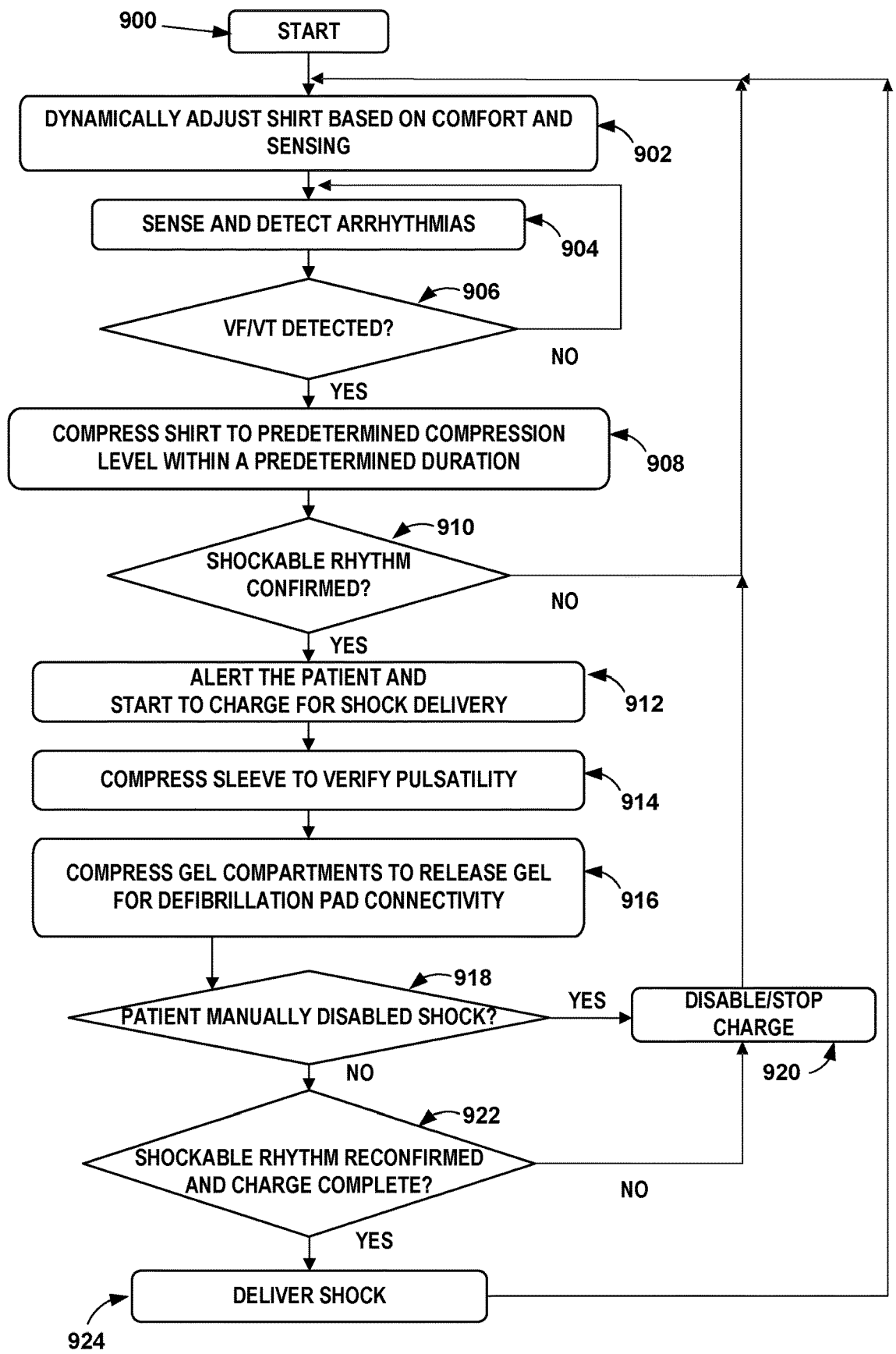
FIG. 9 is a flow diagram illustrating an example operation of a medical device, such as a wearable automated external defibrillator, according to one or more techniques of this disclosure.

FIG. 9 is a flow charge illustrating an example operation of a medical device, such as a wearable automated external defibrillator, according to one or more techniques of this disclosure. The flow diagram of FIG. 9 may be described in terms of FIGS. 2A-2D and 3, unless otherwise noted.

Similar to the description of FIG. 8 above, in the example of FIG. 9, a patient may start (900) by putting on garment 202. Processing circuitry 210 of garment 202 may receive an indication from a mechanical sensor and may dynamically adjust the compression level for garment 202, based on the received indication (902). For example, as described above in relation to FIG. 2A, processing circuitry 210 may adjust the compression level of garment 202 to compensate for changes in activity, posture, donning or removing clothing, sensing noise and so on. In some examples, processing circuitry 210 may retrieve from a memory one or more predetermined target compression levels and adjust the compression level of garment 202 to match a selected target compression level, e.g., within a threshold amount of compression as measured by the mechanical sensor. In some examples, a patient may select one or more levels of comfort such as tight, less tight, least tight, and so on. In some examples, processing circuitry 210 may measure sensing performance and selects the least constricting compression that meets the sensing requirements. In some examples, the selected compression level may include a margin of compression to ensure sensing. In other examples, the selected target compression may be based on some combination, e.g., a selected comfort level, and further adjusted by processing circuitry 210 based on the detected sensing.

As described above in relation to FIG. 8, in some examples processing circuitry 210 may sense and detect a cardiac arrhythmia using ECGs via the electrodes of sensing device 330 (904). In some examples, the arrhythmia may include arrhythmias that garment 202 may not be configured to treat or may be non-dangerous (NO branch of 906). In other examples, processing circuitry 210 may detect a dangerous arrhythmia, such as VT or VF (YES branch of 906).

In response to detecting the cardiac arrhythmia, processing circuitry 210 may cause the compression level to change to a tighter compression level (908). In some examples, processing circuitry 210 may cause the compression level to change to a tighter level within a predetermined duration, e.g., within a few seconds (908).

While at the tighter compression level, processing circuitry 210 may confirm whether the cardiac arrhythmia is treatable by a defibrillation shock. For a short term VT episode, or some other non-shockable rhythm, processing circuitry 210 may not be able to confirm the shockable rhythm (NO branch of 910). In some examples, when processing circuitry 210 is unable to confirm the shockable rhythm, processing circuity 210 may cause the compression level of the garment to reset to a more comfortable compression level for the patient.

In the example of an arrhythmia such as VT or VF, the arrhythmia may be treatable by a defibrillation shock (YES branch of 910). In response to confirming that the cardiac arrhythmia is treatable by the defibrillation shock, processing circuitry 210 may alert patient 208 that the medical device will deliver the defibrillation shock based on the confirmation and therapy generation circuitry 304 may begin charging an electrical energy storage device, to prepare for defibrillation shock delivery (912).

In some examples, processing circuitry 210 may compress the sleeve to verify pulsatility (914) for example, to compare with detected ECG or impedance signals via electrode device 514. Mechanical or other sensors may be configured then determine if there is pulsatility by the sensor waveform. In some examples, processing circuitry 210 may use pulsatility measurements to confirm arrhythmia detection (e.g., a loss of pulsatility) and may avoid unnecessary therapy shocks.

In some examples, therapy delivery electrodes 336 may include associated conductive gel delivery systems, which may improve electrode-to-skin conduction when delivering a defibrillation shock. By including a gel delivery system, the medical system of this disclosure may provide advantages over other types of wearable medical devices. Examples of wearable medical devices that require gels, or other adhesives, as soon as the patient puts on the wearable medical device, may be less comfortable for a patient than the medical system of this disclosure which may include dry electrodes. Delivering a defibrillation shock without some sort of conductive medium, such as a conductive gel, may also be more uncomfortable for a patient when compared to therapy delivery electrodes in contact with the skin that have a conductive medium. Therefore, the medical system of this disclosure may include gel compartments near the therapy delivery electrodes, e.g., defibrillation pads. Processing circuitry 210 may cause the gel compartments to release the gel to improve defibrillation pad connectivity (916). As described above in relation to FIG. 2A, processing circuitry 210 may activate one or more conductive gel release mechanisms prior to delivering the defibrillation shock, e.g., by causing an electrical signal to compress the gel compartments, which may cause the conductive gel to disperse under one or more of the therapy delivery electrodes 230, 232 or 234 to improve conduction between the electrode and the patient's skin.

In some examples, in response to receiving an input from patient 208 to disable the shock (YES branch of 918), processing circuitry may cause the medical device to stop charging and disable delivery of the defibrillation shock (920). In other examples, patient 208 may not disable the shock (NO branch of 918).

Once the charging is complete, processing circuitry 210 may reconfirm that processing circuitry 210 is still receiving an indication of a shockable arrythmia via sensing device 330 (YES branch of 922). In response, the processing circuitry may cause the therapy delivery circuitry, e.g., therapy generation circuitry 304 and therapy delivery electrodes 336 of the medical device to deliver the defibrillation shock (924). In other examples, processing circuitry 210 may not be able to reconfirm the shockable rhythm (NO branch of 922) and stop charging (920).

The techniques of this disclosure may also be described in the following examples.

Example 1: A medical device that includes a first electrode, a second electrode, a third electrode, and a fourth electrode, each of the electrodes configured to be placed in contact with skin of a patient and held in position with a compressive member that is free of adhesives, wherein the first electrode and second electrode are configured to output an impedance measurement signal, and wherein the third electrode and the fourth electrode are configured to sense electrocardiogram (ECG) signals from the patient via the third electrode and the fourth electrode.

Example 2: The medical device of example 1, wherein the first electrode and the third electrode form a concentric arrangement, wherein the third electrode surrounds the first electrode; and wherein the second electrode and the fourth electrode form a concentric arrangement, wherein the fourth electrode surrounds the second electrode.

Example 3: The medical device of examples 1 and 2, wherein the first electrode defines a substantially circular disk shaped electrode and, wherein the third electrode defines a substantially circular ring shaped electrode surrounding the first electrode.

Example 4: The medical device of any combination of examples 1-3, wherein the first electrode and the second electrode define a first dimension, wherein the third electrode and the fourth electrode define a second dimension, and wherein the second dimension is greater than the first dimension.

Example 5: The medical device of any combination of examples 1-4, wherein the first dimension and the second dimension is a diameter.

Example 6: The medical device of any combination of examples 1-5, wherein the first electrode and the third electrode define a geometric shape, wherein the first electrode defines a first portion of the geometric shape with a first surface area in contact with the patient's skin and the third electrode defines a second portion of the geometric shape with a second surface area in contact with the patient's skin, and wherein the first surface area is smaller than the second surface area.

Example 7: The medical device of any combination of examples 1-6, wherein the geometric shape comprises a substantially circular disk, and wherein the first portion comprises a substantially pie shaped portion of the circular disk.

Example 8: The medical device of any combination of examples 1-7, wherein a first distance between the first electrode and the second electrode is smaller than a second distance between the third electrode and the fourth electrode.

Example 9: The medical device of any combination of examples 1-8, wherein the third electrode and the fourth electrode define an area between the third electrode and the fourth electrode, and wherein the first electrode and the second electrode are located in the area.

Example 10: A medical system includes first circuitry configured to measure a voltage, a second circuitry configured output a constant current signal, a medical device includes a first electrode, a second electrode, a third electrode, and a fourth electrode, each of the electrodes configured to be placed in contact with skin of a patient and held in position with a compressive member that is free of adhesives; and sensing circuitry configured to: output an impedance measurement signal via the first electrode and the second electrode; and sense electrocardiogram (ECG) signals from the patient via the third electrode and the fourth electrode.

Example 11: The medical system of example 10, wherein the second circuitry is configured to output the constant current signal at a first time for a predetermined duration, and wherein the first circuitry is further configured to measure a biological impedance during the predetermined duration based on the output constant current signal.

Example 12: The medical system of examples 10 and 11, wherein the first circuitry comprises: a first stage amplifier circuit; a filter circuit; a second stage amplifier circuit; and a peak detector circuit.

Example 13: The medical system of any combination of examples 10-12, further comprising processing circuitry configured to: receive an output from the second stage amplifier circuit; receive an output from the peak detector circuit; determine an electrocardiogram based on the received outputs.

Example 14: The medical system of any combination of examples 10-13, wherein the first electrode and the third electrode form a concentric arrangement, wherein the third electrode surrounds the first electrode; and wherein the second electrode and the fourth electrode form a concentric arrangement, wherein the fourth electrode surrounds the second electrode.

Example 15: The medical system of any combination of examples 10-14, wherein the first electrode and the third electrode define a geometric shape, wherein the first electrode defines a first portion of the geometric shape with a first surface area in contact with the patient's skin and the third electrode defines a second portion of the geometric shape with a second surface area in contact with the patient's skin, and wherein the first surface area is smaller than the second surface area.

Example 16: The medical system of any combination of examples 10-15, wherein the geometric shape comprises a substantially circular disk, and wherein the first portion comprises a substantially pie shaped portion of the circular disk.

Example 17: The medical system of any combination of examples 10-16, wherein a first distance between the first electrode and the second electrode is smaller than a second distance between the third electrode and the fourth electrode.

Example 18: The medical system of any combination of examples 10-17, wherein the third electrode and the fourth electrode define an area between the third electrode and the fourth electrode, and wherein the first electrode and the second electrode are located in the area.

Example 19: A method includes delivering, by a medical device, an impedance measurement signal via a first electrode and a second electrode; sensing, by the medical device, an electrocardiogram via a third electrode and a fourth electrode, wherein each of the first electrode, the second electrode, the third electrode, and the fourth electrode is configured to be placed in contact with skin of a patient and held in position with a compressive member that is free of adhesives.

Example 20: The method of example 19, wherein the first electrode and the third electrode form a concentric arrangement, wherein the third electrode surrounds the first electrode; and wherein the second electrode and the fourth electrode form a concentric arrangement, wherein the fourth electrode surrounds the second electrode.

Example 21: The method of examples 19-20, wherein the first electrode defines a substantially circular disk shaped electrode and, wherein the third electrode defines a substantially circular ring shaped electrode surrounding the first electrode.

Example 22: A method includes receiving, by processing circuitry, an indication from a mechanical sensor of a compression level for a garment, wherein a medical device comprises the garment, the processing circuitry, and the mechanical sensor; setting, by the processing circuitry, the compression level for the garment to a first compression level at a first time, wherein the garment comprises a plurality of electrodes, and wherein the first compression level locates the plurality of electrodes on a patient's skin such that the plurality of electrodes receives bioelectrical signals from a patient; and at a second time, changing, by the processing circuitry, the compression level from the first level to a second compression level based on one or more of: the indication of the compression level from the mechanical sensor and the received bioelectrical signals from the plurality of electrodes.

Example 23: The method of example 22, further comprising a motion sensor, wherein the processing circuitry is further configured to dynamically adjust the compression level of the garment based on one or more of: the indication of the compression level from the mechanical sensor, the received bioelectrical signals or the indication from the motion sensor.

Example 24: The method of any combination of examples 22-23, wherein the one or more bioelectrical signals comprise: an electrocardiogram of the patient, and a biological impedance of the patient.

Example 25: The method of any combination of examples 22-24, wherein the received bioelectrical signal comprises a biological impedance of the patient.

Example 26: The method of any combination of examples 22-25, wherein the received bioelectrical signal comprises an electrocardiogram of the patient.

Example 27: The method of any combination of examples 22-26, further includes detecting, by the processing circuitry, a cardiac arrhythmia based on the received bioelectrical signals; in response to detecting the cardiac arrhythmia, changing the compression level to the second compression level, wherein the second compression level is tighter than the first compression level, while at the second compression level, confirming, by the processing circuitry, that the cardiac arrhythmia is treatable by a defibrillation shock; in response to confirming that the cardiac arrhythmia is treatable by the defibrillation shock, alerting the patient that the medical device will deliver the defibrillation shock based on the confirmation; and causing, by the processing circuitry, therapy delivery circuitry of the medical device to deliver the defibrillation shock.

Example 28: The method of any combination of examples 22-27, wherein the cardiac arrhythmia is one of ventricular fibrillation (VF) or ventricular tachycardia (VT).

Example 29: The method of any combination of examples 22-28, wherein alerting the patient comprises causing, by the processing circuitry the compression level to change between two or more compression levels.

Example 30: The method of any combination of examples 22-29, wherein changing the compression level to the second compression level causes the one or more conductive gel compartments to release the conductive gel.

Example 31: The method of any combination of examples 22-29, further comprising, before causing the therapy delivery circuitry to deliver the defibrillation shock, causing, by the processing circuitry, one or more conductive gel compartments associated with one or more therapy delivery electrodes to release conductive gel.

Example 32: The method of any combination of examples 22-30, further includes before causing the therapy delivery circuitry to deliver the defibrillation shock, receiving, by the processing circuitry, an indication from the patient to disable delivery of the defibrillation shock; and in response to receiving the indication from the patient, disabling the delivery of the defibrillation shock.

Example 33: A medical device includes a garment configured to be worn by a patient, the garment including: a mechanical sensor configured to output an indication of a compression level of the garment; an apparatus configured to adjust the compression level of the garment; and a plurality of electrodes located on the garment such that the plurality of electrodes receives bioelectrical signals from a patient's skin; processing circuitry attached to the garment and operatively coupled to the mechanical sensor, the plurality of electrodes and the apparatus, wherein the processing circuitry is configured to: receive the indication from the mechanical sensor of the compression level for the garment, set the compression level for the garment to a first compression level at a first time based on the indicated compression level; at a second time, change the compression level from the first compression level to a second compression level based on one or more of: the indication of the compression level from the mechanical sensor and the received bioelectrical signals from the plurality of electrodes.

Example 34: The medical device of example 32, further comprising a motion sensor, wherein the processing circuitry is further configured to dynamically adjust the compression level of the garment based on one or more of: the indication of the compression level from the mechanical sensor, the received bioelectrical signals or the indication from the motion sensor.

Example 35: The medical device of examples 32 and 33, wherein the processing circuitry is further configured to: detect a cardiac arrhythmia based on the received bioelectrical signals; change the compression level to the second compression level, wherein the second compression level is tighter than the first compression level, confirm that the cardiac arrhythmia is treatable by a defibrillation shock; alert the patient that the therapy delivery circuitry will deliver the defibrillation shock; cause therapy delivery circuitry to deliver the defibrillation shock.

Example 36: The medical system of any combination of examples 32-34, wherein alerting the patient comprises causing, by the processing circuitry the compression level to change between two or more compression levels.

Example 37: The medical device of any combination of examples 32-35, wherein the processing circuitry is further configured to: before causing the therapy delivery circuitry to deliver the defibrillation shock, receive an indication from the patient to disable delivery of the defibrillation shock; and in response to receiving the indication from the patient, disable the delivery of the defibrillation shock.

Example 38: The medical device of any combination of examples 32-36, wherein confirming that the cardiac arrhythmia is treatable by a defibrillation shock is based at least in part on bioelectrical signals sensed while at the second compression level.

Example 39: The medical device of any combination of examples 32-37, wherein the processing circuitry is further configured to, before causing the therapy delivery circuitry to deliver the defibrillation shock, cause one or more conductive gel compartments associated with one or more therapy delivery electrodes to release conductive gel.

Example 40: The medical device of any combination of examples 32-38, wherein changing the compression level to the second compression level causes the one or more conductive gel compartments to release the conductive gel.

Example 41: The medical device of any combination of examples 32-39, wherein the one or more bioelectrical signals comprise a biological impedance of the patient.

Example 42: The medical device of any combination of examples 32-40, wherein the one or more bioelectrical signals comprises an electrocardiogram of the patient.

Example 43: The medical device of any combination of examples 32-39, wherein the one or more bioelectrical signals comprise: an electrocardiogram of the patient, and a biological impedance of the patient.

Example 44: A computer-readable medium comprising instructions for causing a programmable processor to: receive an indication, from a mechanical sensor of a medical device, of a compression level for a garment, wherein the medical device comprises the garment, the programmable processor and the mechanical sensor; set the compression level for the garment to a first compression level at a first time, wherein the garment comprises a plurality of electrodes, and wherein the first compression level locates the plurality of electrodes on a patient's skin such that the plurality of electrodes receives bioelectrical signals from a patient; and at a second time different from the first time, change the compression level from the first compression level to a second compression level based on one or more of: the indication of the compression level from the mechanical sensor and the received bioelectrical signals.

Various examples of the disclosure have been described. These and other examples are within the scope of the following claims.

What is claimed is:

1. A medical device comprising:
a first electrode, a second electrode, a third electrode, and a fourth electrode, each of the electrodes configured to be placed in contact with skin of a patient and held in position with a compressive member that is free of adhesives,
wherein the third electrode surrounds the first electrode,
wherein the fourth electrode surrounds the second electrode,
wherein the first electrode and second electrode are configured to output an impedance measurement signal,
wherein the impedance measurement signal is configured to induce a voltage on the skin of the patient, and
wherein the third electrode and the fourth electrode are configured to:
sense the induced voltage and conduct the induced voltage to circuitry configured to determine a biological impedance for the patient based on the sensed voltage from the third electrode and the fourth electrode;
sense electrocardiogram (ECG) signals from the patient via the third electrode and the fourth electrode, wherein the circuitry is configured to simultaneously sense the ECG and determine the biological impedance.

2. The medical device of claim 1, wherein the first electrode and the third electrode form a concentric arrangement, and wherein the second electrode and the fourth electrode form a concentric arrangement.

3. The medical device of claim 1,
wherein the first electrode defines a substantially circular disk shaped electrode, and,
wherein the third electrode defines a substantially circular ring shaped electrode surrounding the first electrode.

4. The medical device of claim 1,
wherein the first electrode and the second electrode define a first dimension,
wherein the third electrode and the fourth electrode define a second dimension, and
wherein the second dimension is greater than the first dimension.

5. The medical device of claim 4, wherein the first dimension and the second dimension are diameters.

6. The medical device of claim 1,
wherein the first electrode and the third electrode define a geometric shape,
wherein the first electrode defines a first portion of the geometric shape with a first surface area configured to be in contact with the patient's skin and the third electrode defines a second portion of the geometric shape with a second surface area configured to be in contact with the patient's skin, and wherein the first surface area is smaller than the second surface area.

7. The medical device of claim 1, wherein a first distance between the first electrode and the second electrode is smaller than a second distance between the third electrode and the fourth electrode.

8. The medical device of claim 7, wherein the medical device is configured to initiate determination of the biological impedance periodically and/or in response to an event.

9. A medical system comprising:
a medical device comprising a first electrode, a second electrode, a third electrode, and a fourth electrode, each of the electrodes configured to be placed in contact with skin of a patient and held in position with a compressive member that is free of adhesives,
wherein the third electrode surrounds the first electrode,
wherein the fourth electrode surrounds the second electrode, first circuitry configured to output an impedance measurement signal via the first and second electrodes and induce a voltage on the skin of the patient, second circuitry configured to measure the induced voltage via the third and fourth electrodes, and processing circuitry configured to:
- receive an output from the second circuitry,
- determine a biological impedance for the patient based on the received output; and
- detect electrocardiogram (ECG) signals from the patient based on the received output simultaneously with determining the biological impedance.

10. The medical system of claim 9,
wherein the first circuitry is configured to output the impedance measurement signal at a first time for a predetermined duration, and
wherein the second circuitry is further configured to measure the biological impedance during the predetermined duration based on the output impedance measurement signal.

11. The medical system of claim 9, wherein the first circuitry comprises:
a first stage amplifier circuit;
a filter circuit;
a second stage amplifier circuit; and
a peak detector circuit.

12. The medical system of claim 11, wherein the processing circuitry is configured to:
receive an output from the second stage amplifier circuit;
receive an output from the peak detector circuit;
determine the electrocardiogram based on the received outputs.

13. The medical system of claim 9,
wherein the first electrode and the third electrode form a concentric arrangement,
wherein the second electrode and the fourth electrode form a concentric arrangement.

14. The medical system of claim 9,
wherein the first electrode and the third electrode define a geometric shape,
wherein the first electrode defines a first portion of the geometric shape with a first surface area in contact with the skin of the patient and the third electrode defines a second portion of the geometric shape with a second surface area in contact with the skin of the patient and,
wherein the first surface area is smaller than the second surface area.

15. The medical system of claim 9, wherein a first distance between the first electrode and the second electrode is smaller than a second distance between the third electrode and the fourth electrode.

16. The medical system of claim 15, wherein the medical device is configured to initiate determination of the biological impedance periodically and/or in response to an event.

17. A method comprising;
delivering, by first circuitry of a medical device, an impedance measurement signal via a first electrode and a second electrode, wherein the impedance measurement signal is configured to induce a voltage on skin of a patient;
sensing, by second circuitry of the medical device, the induced voltage via third electrode and a fourth electrode,
wherein each of the first electrode, the second electrode, the third electrode, and the fourth electrode is configured to be placed in contact with the skin of the patient and held in position with a compressive member that is free of adhesives,
wherein the third electrode surrounds the first electrode,
wherein the fourth electrode surrounds the second electrode,
receiving, by processing circuitry of the medical device, an output from the second circuitry;
determining, by the processing circuitry, a biological impedance of the patient based at least on the received output; and
measuring and analyzing, by the processing circuitry, an electrocardiogram of the patient based on the received output, wherein the processing circuitry is configured to simultaneously measure the electrocardiogram and determine the biological impedance.

18. The method of claim 17, wherein the medical device is configured to initiate determination of the biological impedance periodically and/or in response to an event.

* * * * *